(12) United States Patent
Fukuda et al.

(10) Patent No.: US 11,769,250 B2
(45) Date of Patent: Sep. 26, 2023

(54) MEDICAL CARE SUPPORT DEVICE, MEDICAL CARE SUPPORT METHOD, AND MEDICAL CARE SUPPORT PROGRAM

(71) Applicant: FUJIFILM Corporation, Tokyo (JP)

(72) Inventors: Takeshi Fukuda, Kanagawa (JP); Haruyasu Nakatsugawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 410 days.

(21) Appl. No.: 17/015,461

(22) Filed: Sep. 9, 2020

(65) Prior Publication Data

US 2021/0073985 A1 Mar. 11, 2021

(30) Foreign Application Priority Data

Sep. 11, 2019 (JP) ................................ 2019-165767

(51) Int. Cl.
*G06T 7/00* (2017.01)
*G16H 30/40* (2018.01)
*G16H 10/60* (2018.01)
*G16H 50/20* (2018.01)
(Continued)

(52) U.S. Cl.
CPC .......... *G06T 7/0012* (2013.01); *A61B 5/4504* (2013.01); *A61B 5/746* (2013.01); *G16H 10/60* (2018.01); *G16H 30/40* (2018.01); *G16H 50/20* (2018.01); *G16H 50/30* (2018.01); *A61B 2503/40* (2013.01); *G06T 2207/10081* (2013.01); *G06T 2207/10088* (2013.01); *G06T 2207/20084* (2013.01); *G06T 2207/30008* (2013.01)

(58) Field of Classification Search
CPC ......... G06T 7/0012; G06T 2207/10081; G06T 2207/10088; G06T 2207/20084; G06T 2207/30008; G16H 10/60; G16H 50/30; G16H 50/20; G16H 30/40; A61B 5/4504; A61B 5/746; A61B 2503/40
See application file for complete search history.

(56) References Cited

U.S. PATENT DOCUMENTS

| 2007/0274584 A1* | 11/2007 | Leow ..................... G03B 42/02 382/132 |
| 2018/0020999 A1 | 1/2018 | Yamamoto |
| 2018/0247020 A1* | 8/2018 | Itu .......................... G16H 10/60 |

FOREIGN PATENT DOCUMENTS

JP    2014064776 A  *  4/2014
WO   WO 2016/129682 A1   8/2016

* cited by examiner

*Primary Examiner* — Vu Le
*Assistant Examiner* — Winta Gebreslassie
(74) *Attorney, Agent, or Firm* — Birch, Stewart, Kolasch & Birch, LLP

(57) ABSTRACT

A medical care support device includes an acquisition unit that acquires medical information including medical image data representing a medical image obtained by imaging a bone of a subject and age information representing an age of the subject in a case where the medical image is imaged, a derivation unit that derives presence or absence of a fracture in a growth plate of the subject, based on the medical information acquired by the acquisition unit and a learned model learned in advance using a plurality of pieces of learning medical information including the medical image data and the age information, and a warning information output unit that outputs warning information representing a warning in a case where the growth plate of the subject is fractured.

8 Claims, 34 Drawing Sheets

(51) Int. Cl.
*G16H 50/30* (2018.01)
*A61B 5/00* (2006.01)

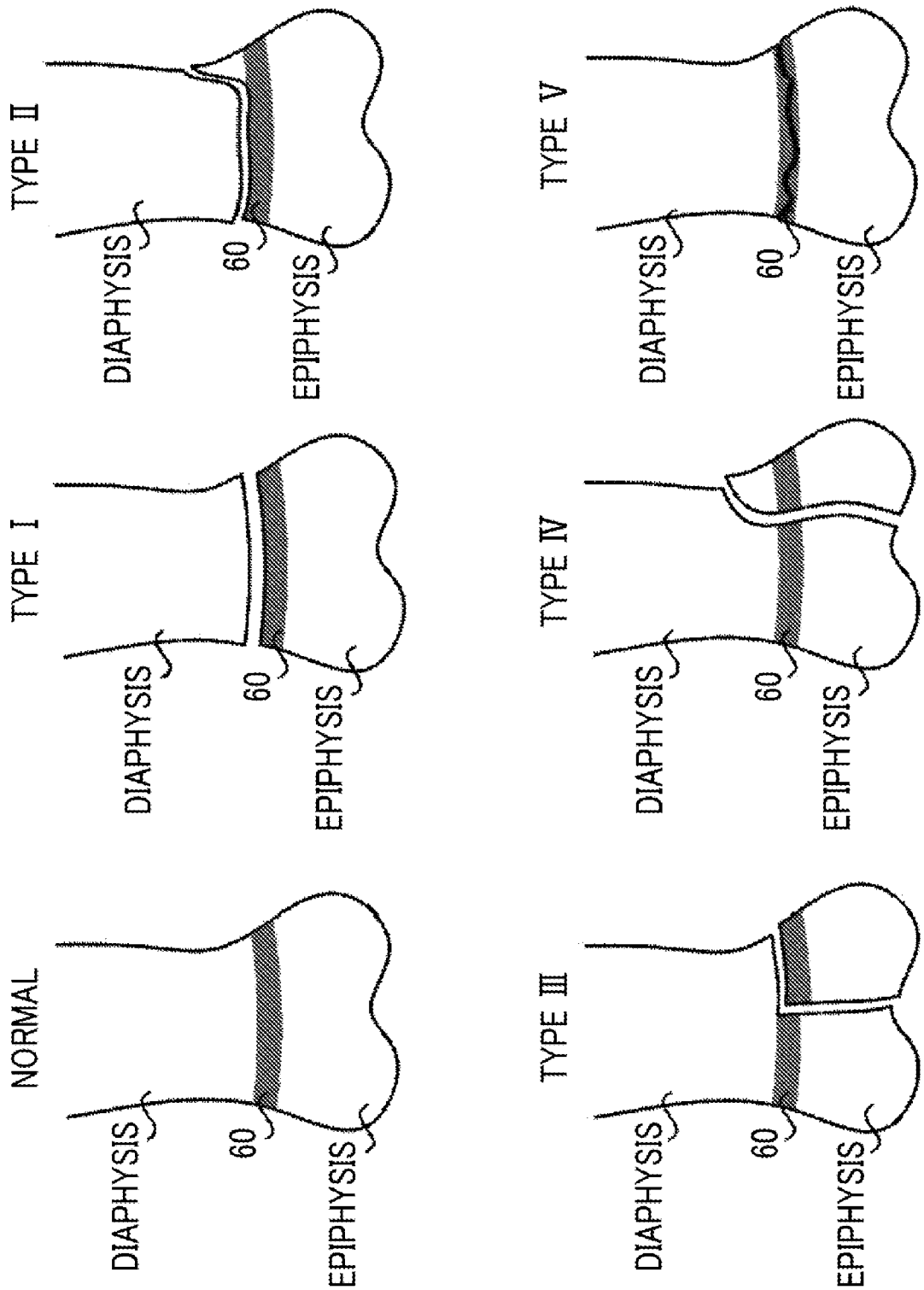

MEDICAL CARE SUPPORT DEVICE, MEDICAL CARE SUPPORT METHOD, AND MEDICAL CARE SUPPORT PROGRAM

CROSS-REFERENCE TO RELATED APPLICATIONS

The present application claims priority under 35 U.S.C. § 119 to Japanese Patent Application No. 2019-165767 filed on Sep. 11, 2019. The above application is hereby expressly incorporated by reference, in its entirety, into the present application.

BACKGROUND

1. Technical Field

The present disclosure relates to a medical care support device, a medical care support method, and a medical care support program.

2. Description of the Related Art

In general, a doctor diagnoses the presence or absence of a fracture using a medical image of a subject. As a technique of detecting the fracture from the medical image instead of the doctor, for example, WO2016/129682A discloses a technique of evaluating a risk of the fracture in a subject based on a tomosynthesis image of the subject.

SUMMARY

By the way, the fracture of a growth plate may be a factor that hinders growth of the subject. Therefore, appropriate medical care such as early detection is important for the fracture in the growth plate.

However, the technique described in WO2016/129682A evaluates the risk of the fracture, but does not detect the fracture itself. The technique described in WO2016/129682A may not be sufficient to deal with the fracture related to the growth plate. Therefore, there is a need for a technique that supports medical care for the fracture in the growth plate using the medical image.

The present disclosure has been made in view of the above circumstances, and a purpose thereof is to provide a medical care support device, a medical care support method, and a medical care support program capable of effectively supporting medical care for a fracture of a growth plate using a medical image.

In order to achieve the above object, a medical care support device according to a first aspect of the present disclosure comprises an acquisition unit that acquires medical information including medical image data representing a medical image obtained by imaging a bone of a subject and age information representing an age of the subject in a case where the medical image is imaged, a derivation unit that derives presence or absence of a fracture in a growth plate of the subject, based on the medical information acquired by the acquisition unit and a learned model learned in advance using a plurality of pieces of learning medical information including the medical image data and the age information, and a warning information output unit that outputs warning information representing a warning in a case where the growth plate of the subject is fractured.

In the medical care support device according to a second aspect of the present disclosure, the medical information further includes breed information representing a breed of the subject, and the learning medical information further includes the breed information, in the medical care support device according to the first aspect.

In the medical care support device according to a third aspect of the present disclosure, the medical information further includes thickness information representing a thickness of the bone of the subject, and the learning medical information further includes the thickness information, in the medical care support device according to the first aspect.

In the medical care support device according to a fourth aspect of the present disclosure, the medical information further includes body type information on a body type of the subject, and the learning medical information further includes the body type information, in the medical care support device according to the first aspect.

In the medical care support device according to a fifth aspect of the present disclosure, the medical information further includes action information on an action of the subject, and the learning medical information further includes the action information, in the medical care support device according to the first aspect.

In the medical care support device according to a sixth aspect of the present disclosure, the medical image data included in the learning medical information includes first medical image data representing a first medical image in which the growth plate is fractured and second medical image data representing a second medical image in which the growth plate is not fractured, in the medical care support device according to the first aspect.

In the medical care support device according to a seventh aspect of the present disclosure, the medical image data included in the learning medical information includes, out of the growth plates in a pair of left and right bones, first medical image data in which the growth plate of one bone is fractured and second medical image data in which the growth plate of the other bone is not fractured, and the acquisition unit acquires the medical image data representing the medical image obtained by imaging each of the pair of left and right bones as the medical image data of the subject, in the medical care support device according to the first aspect.

In order to achieve the above object, a medical care support method according to an eighth aspect of the present disclosure executed by a computer comprises acquiring medical information including medical image data representing a medical image obtained by imaging a bone of a subject and age information representing an age of the subject in a case where the medical image is imaged, deriving presence or absence of a fracture in a growth plate of the subject, based on the acquired medical information and a learned model learned in advance using a plurality of pieces of learning medical information including the medical image data and the age information, and outputting warning information representing a warning in a case where the growth plate of the subject is fractured.

In order to achieve the above object, a non-transitory computer-readable storage medium storing a medical care support program according to a ninth aspect of the present disclosure causes a computer to execute the following processing of acquiring medical information including medical image data representing a medical image obtained by imaging a bone of a subject and age information representing an age of the subject in a case where the medical image is imaged, deriving presence or absence of a fracture in a growth plate of the subject, based on the acquired medical information and a learned model learned in advance using a plurality of pieces of learning medical information including the medical image data and the age information, and outputting warning information representing a warning in a case where the growth plate of the subject is fractured.

The medical care support device according to the present disclosure comprises a memory that stores a command to be executed by a computer, and a processor configured to execute the stored command. The processor acquires medical information including medical image data representing a medical image obtained by imaging a bone of a subject and age information representing an age of the subject in a case where the medical image is imaged, derives presence or absence of a fracture in a growth plate of the subject, based on the acquired medical information and a learned model learned in advance using a plurality of pieces of learning medical information including the medical image data and the age information, and outputs warning information representing a warning in a case where the growth plate of the subject is fractured.

According to the present disclosure, it is possible to effectively support medical care for a fracture of a growth plate using a medical image.

BRIEF DESCRIPTION OF THE DRAWINGS

FIG. 35 is a diagram for describing types of fractures of the growth plate.

DETAILED DESCRIPTION

Hereinafter, an embodiment for implementing a technique of the present disclosure will be described in detail with reference to drawings. In the following embodiment, a case where a "dog" is employed as a subject will be described.

First Embodiment

Figure 1:
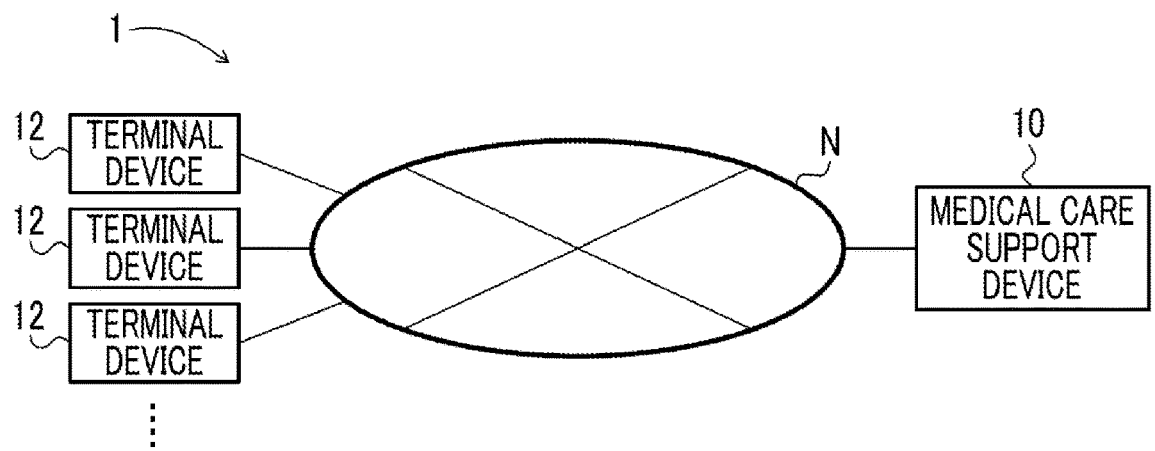
FIG. 1 is a block diagram showing an example of a configuration of a medical care support system according to a first embodiment.

First, a medical care support system 1 according to the present embodiment will be described with reference to FIG. 1. FIG. 1 is a block diagram representing an example of a configuration of the medical care support system 1 according to the present embodiment. As shown in FIG. 1, the medical care support system 1 according to the present embodiment comprises a medical care support device 10 and a plurality (three in FIG. 1 as an example) of terminal devices 12. The medical care support device 10 and the plurality of terminal devices 12 are respectively connected to a network N and can communicate with each other through the network N.

The medical care support device 10 is installed in, for example, an animal hospital. An example of the medical care support device 10 includes a server computer. The medical care support device 10 may be a cloud server. The terminal device 12 is installed in, for example, the animal hospital and used by a user such as a veterinarian. Examples of the terminal device 12 include a personal computer and a tablet computer.

Figure 2:
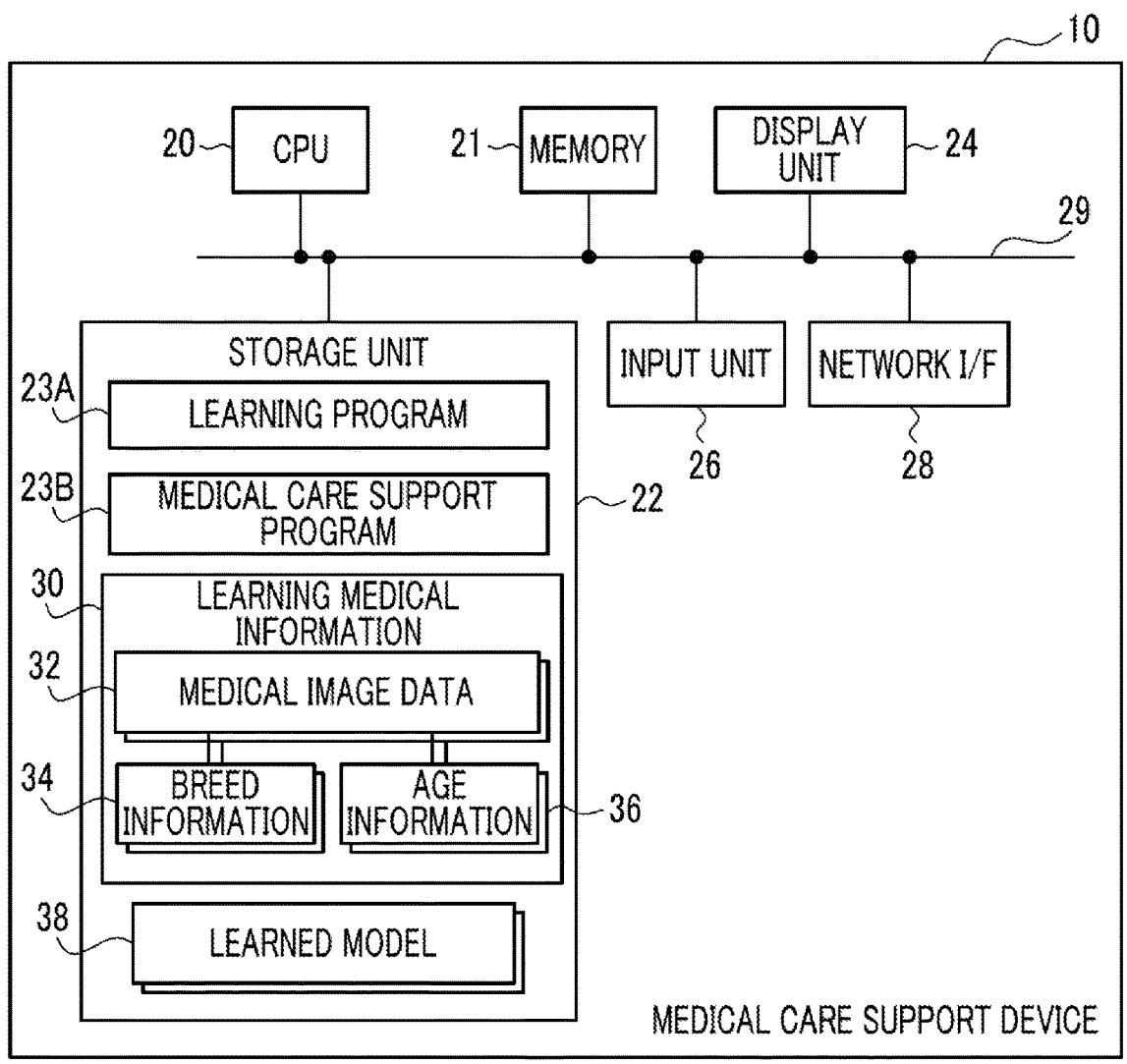
FIG. 2 is a block diagram showing an example of a hardware configuration of a medical care support device according to the first embodiment.

Next, an example of a hardware configuration of the medical care support device 10 according to the present embodiment will be described with reference to FIG. 2. As shown in FIG. 2, the medical care support device 10 includes a central processing unit (CPU) 20, a memory 21 as a temporary storage area, and a nonvolatile storage unit 22. The medical care support device 10 includes a display unit 24 such as a liquid crystal display, an input unit 26 such as a keyboard or a mouse, and a network interface (I/F) 28 connected to the network N. The display unit 24 and the input unit 26 may be integrated as a touch panel display. The CPU 20, the memory 21, the storage unit 22, the display unit 24, the input unit 26, and the network I/F 28 are connected to a bus 29 communicably with each other.

The storage unit 22 is formed by a hard disk drive (HDD), a solid state drive (SSD), a flash memory, and the like. The storage unit 22 as a storage medium stores a learning program 23A. The CPU 20 reads out the learning program 23A from the storage unit 22, develops the program in the memory 21, and executes the developed learning program 23A. The storage unit 22 stores a medical care support program 23B. The CPU 20 reads out the medical care support program 23B from the storage unit 22, develops the program in the memory 21, and executes the developed medical care support program 23B.

The storage unit 22 according to the present embodiment stores learning medical information 30 and a learned model 38 learned using the learning medical information 30.

Figure 3:
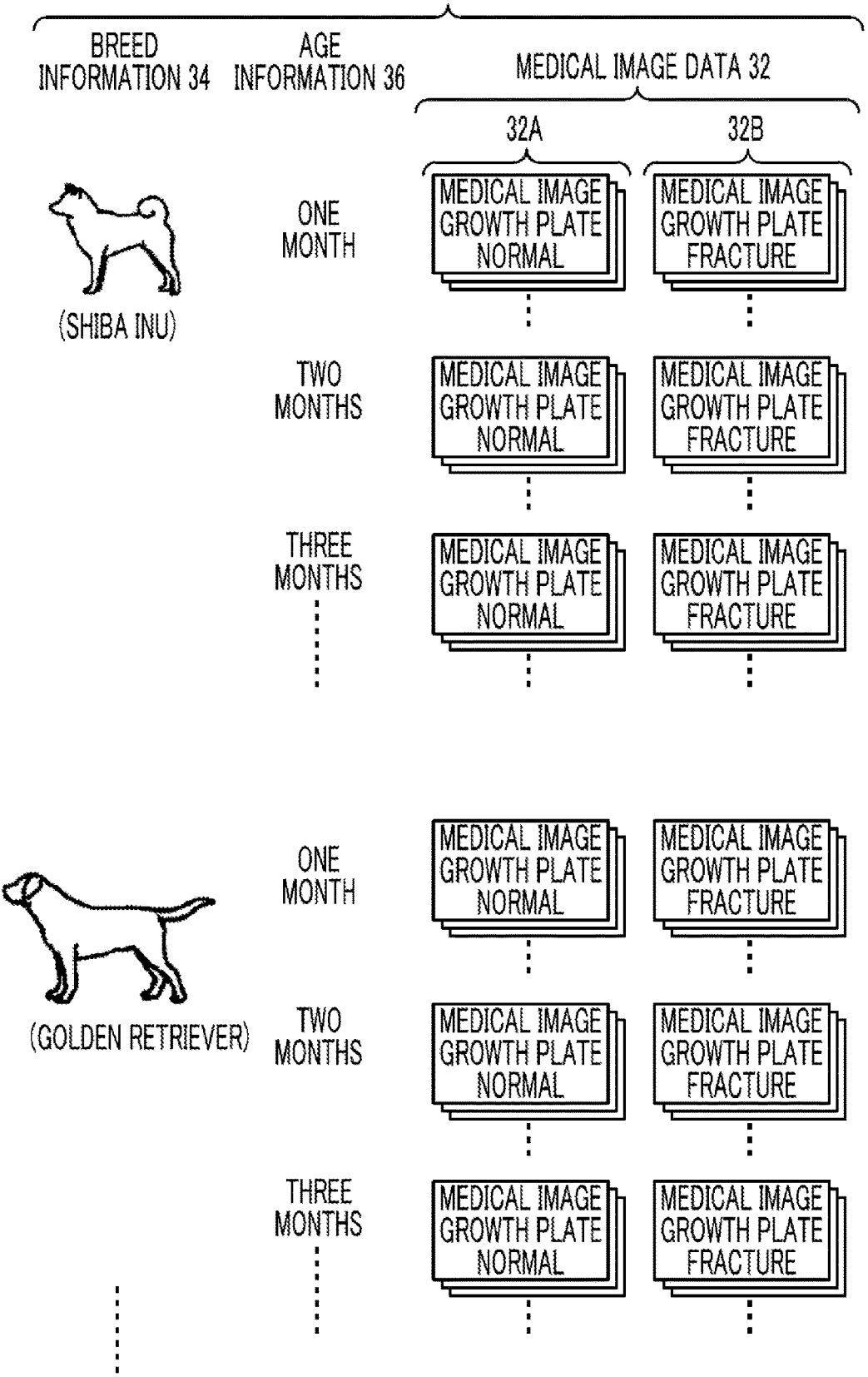
FIG. 3 is a diagram for describing an example of learning medical information according to the first embodiment.

As shown in FIGS. 2 and 3, the learning medical information 30 according to the present embodiment includes medical image data 32, breed information 34, and age information 36, as an example.

The medical image data 32 is image data representing a medical image 33 (refer to FIGS. 4A and 4B) obtained by imaging a portion including a growth plate in a dog bone as the subject using a medical image capturing device. The growth plate is also referred to as a growth line, an epiphyseal plate, and an epiphyseal cartilage, and is a tissue that extends a long tubular bone in a long axis direction by proliferation and enlargement of a cartilage cell with a metaphysis as a proximal boundary and an epiphysis as a distal boundary. The growth plate is found, for example, at a humeral proximal epiphysis, a distal metacarpal epiphysis, a femoral head, a distal femoral epiphysis, and a distal tibial epiphysis. As the subject grows, the growth plate closes and bone growth ends. A time (age) at which the growth plate closes may differ depending on the bone.

The growth plate is a tissue that is fragile compared with other portions of the bone and easily fractured in a case where impact is applied. In a case where the growth plate is fractured, the growth of a bone having the fractured growth plate may be hindered. Therefore, symptoms such as shortening or bending of the bone of the subject and causing persistent pain may occur. In the case where the growth plate is fractured, it is important to perform appropriate medical treatment at an early stage.

An example of the medical image data 32 according to the present embodiment will be described with reference to FIGS. 4A and 4B. In the present embodiment, an embodiment of employing image data representing a radiographic image according to a radiation amount detected by a radiation detector that irradiates the dog of the subject with radiation and detects radiation transmitted through the dog will be described as the medical image data 32. The medical image data 32 may be image data representing a magnetic resonance imaging (MRI) image, image data representing a computed tomography (CT) image, or the like.

Figure 4A:
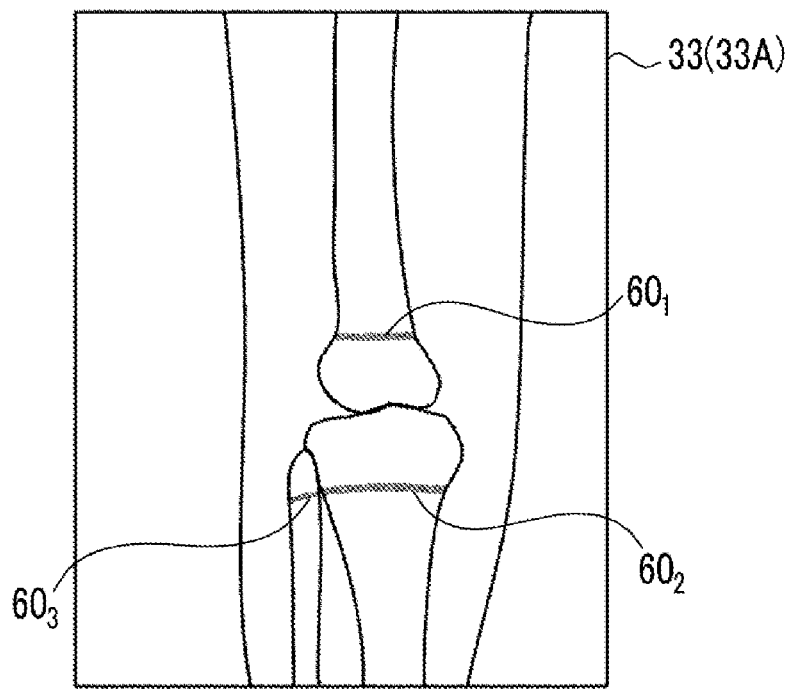
FIG. 4A is a diagram showing an example of a medical image in which growth plates in a non-fractured state are imaged.
Figure 4B:
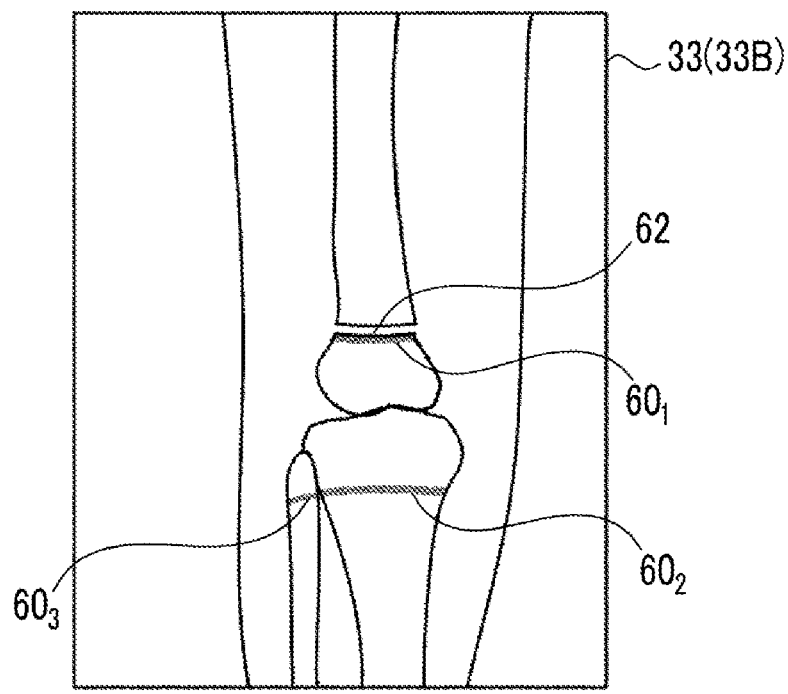
FIG. 4B is a diagram showing an example of a medical image in which a growth plate in a fractured state is imaged.

FIG. 4A shows a medical image 33A in which growth plates $60_1$ to $60_3$ in a non-fractured state are imaged. The medical image 33A is represented by medical image data 32A. FIG. 4B shows a medical image 33B in which the growth plate $60_1$ in a fractured state is imaged. The medical image 33B is represented by medical image data 32B.

In the medical image 33B, the growth plate $60_1$ of the distal femoral epiphysis in a fractured state is imaged, and a fracture portion of the growth plate $60_1$ is shown as a fracture portion 62. In the medical image 33B, the growth plate $60_2$ of a proximal tibial epiphysis and the growth plate $60_3$ of a proximal fibular epiphysis in a non-fractured state are imaged.

As described above, the medical image data 32 according to the present embodiment includes respectively a plurality of pieces of the medical image data 32A representing the medical image 33A in which the growth plate in a fractured state is imaged and a plurality of pieces of the medical image data 32B representing the medical image 33B in which the growth plate in a non-fractured state is imaged. The medical image 33A according to the present embodiment is an example of a second medical image of the present disclosure, and the medical image data 32A according to the present embodiment is an example of second medical image data of the present disclosure. The medical image 33B according to the present embodiment is an example of a first medical image of the present disclosure, and the medical image data 32B according to the present embodiment is an example of first medical image data of the present disclosure.

As shown in FIG. 3 as an example, information representing the presence or absence of the fracture of the imaged growth plate (hereinafter referred to as "fracture presence or absence information") is added to the medical image data 32 according to the present embodiment. In the example of the fracture presence or absence information in FIG. 3, the fact that the growth plate is not fractured is denoted as "normal", and the fact that the growth plate is fractured is denoted as "fracture".

The breed information 34 is breed information representing a breed of the dog which is the subject and is added to the medical image data 32. Specifically, the breed information 34 is information representing a dog breed since the subject is the dog. In the embodiment, the "breed" includes a concept of species such as "dog" and "cat" in addition to the breed such as "dog breed".

The age information 36 is age information representing an age of the dog which is the subject and is added to the medical image data 32. The age information 36 is information representing an elapsed time from birth of the subject. In the present embodiment, the age is referred to for convenience, but an elapsed time in month units, that is, a month age is employed instead of an elapsed time in year units from the birth. As described above, it is preferable to perform the medical treatment for the fracture in the growth plate at an early stage. Therefore, for example, in a case where the growth is relatively fast, such as the dog, the age in year units may not be enough to deal with a bone change due to the growth (influence due to the fracture in the growth plate). Therefore, in the present embodiment, information representing the month age is employed as the age information 36 as described above. As described above, the elapsed time from the birth of the subject represented by the age information 36 is preferably determined according to a growth rate of the bone of the subject, and is not limited to the age or the month age, and may be, for example, a day age.

Figure 5:
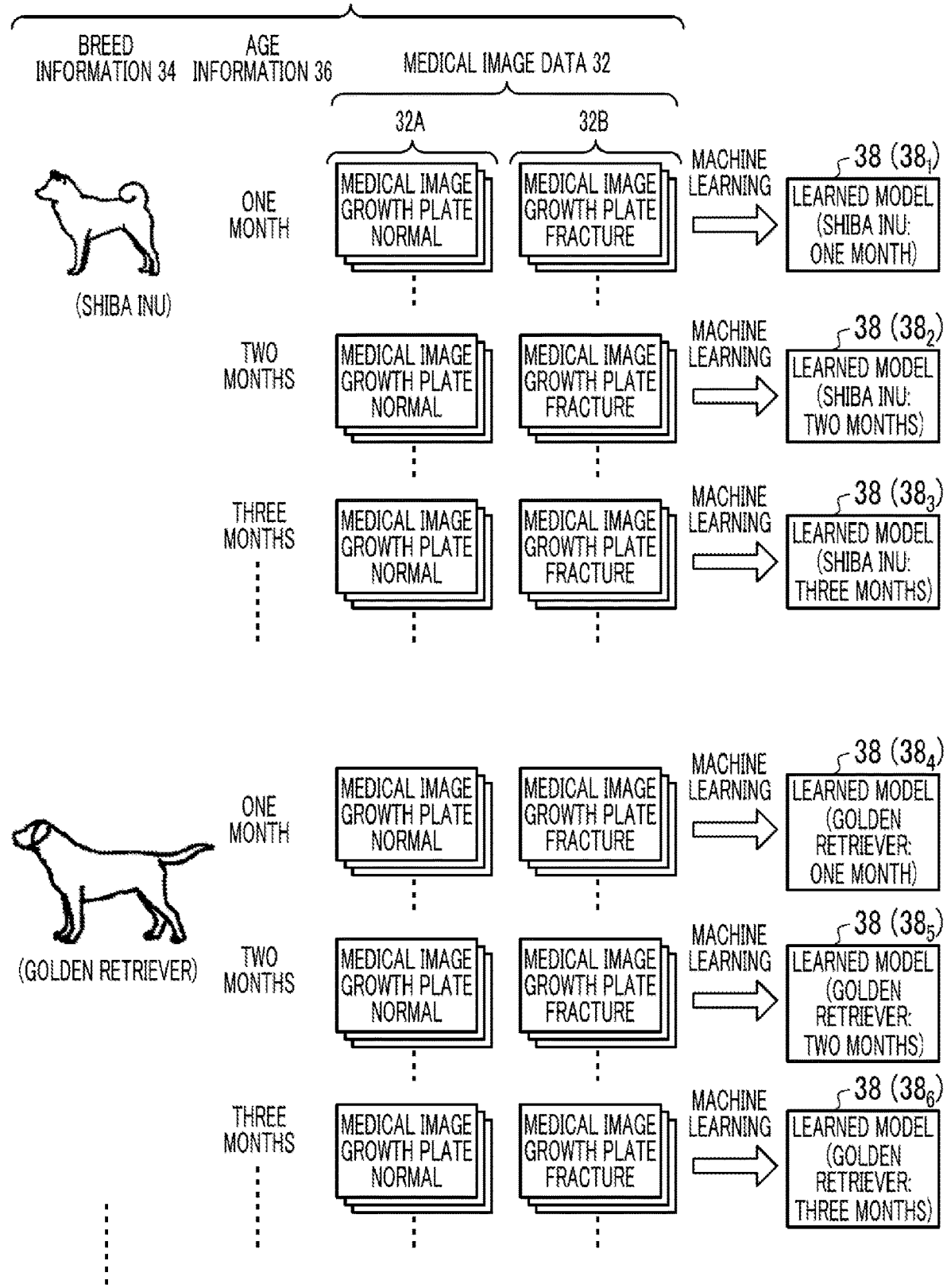
FIG. 5 is a diagram for describing a learned model of the first embodiment.

The learned model 38 is a model learned in advance using the learning medical information 30. In the present embodiment, the learned model 38 is generated by machine learning using the learning medical information 30 as shown in FIG. 5 as an example. For example, in a case where the dog breed represented by the breed information 34 is "Shiba Inu", a learned model $38_1$ for which the dog breed is Shiba Inu and the age is one month is generated from the medical image data 32A and 32B whose age represented by the age information 36 is "one month", as shown in FIG. 5. A learned model $38_2$ for which the dog breed is Shiba Inu and the age is two months is generated from the medical image data 32A and 32B whose age represented by the age information 36 is "two months". A learned model $38_3$ for which the dog breed is Shiba Inu and the age is three months is generated from the medical image data 32A and 32B whose age represented by the age information 36 is "three months".

For example, in a case where the dog breed represented by the breed information 34 is "Golden Retriever", a learned model $38_4$ for which the dog breed is Golden Retriever and the age is one month is generated from the medical image data 32A and 32B whose age represented by the age information 36 is "one month", as shown in FIG. 5. A learned model $38_5$ for which the dog breed is Golden Retriever and the age is two months is generated from the medical image data 32A and 32B whose age represented by the age information 36 is "two months". A learned model $38_6$ for which the dog breed is Golden Retriever and the age is three months is generated from the medical image data 32A and 32B whose age represented by the age information 36 is "three months". An example of the learned model 38 includes a neural network model.

FIG. 5 shows the learned models $38_1$ to $38_6$ in the case where the dog breeds are "Shiba Inu" and "Golden Retriever" and the ages are "one month" to "three months". However, the dog breed and the age are not limited thereto. In a case where the learned models $38_1$ to $38_6$ are collectively referred to without distinction, the symbols "1" to "6" for distinguishing the individual models are omitted and the models are referred to as "learned model 38".

Figure 6:
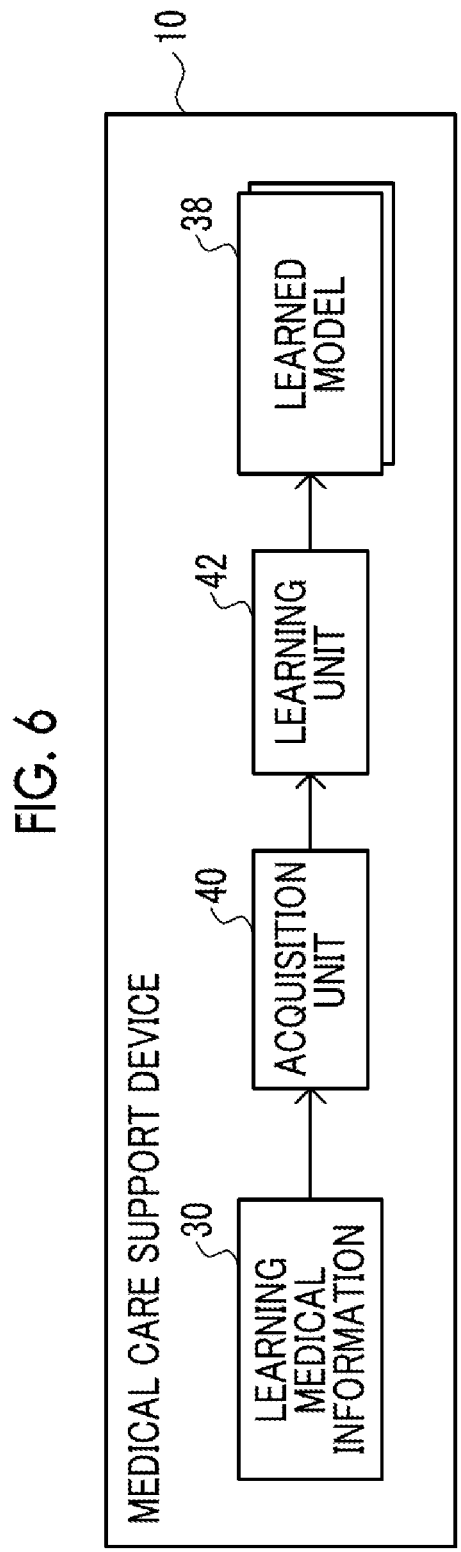
FIG. 6 is a block diagram showing an example of a functional configuration in a learning phase of the medical care support device according to the first embodiment.

Next, a functional configuration in a learning phase of the medical care support device 10 according to the present embodiment will be described with reference to FIG. 6. As shown in FIG. 6, the medical care support device 10 includes an acquisition unit 40 and a learning unit 42. The CPU 20 executes the learning program 23A to function as the acquisition unit 40 and the learning unit 42.

The acquisition unit 40 acquires the learning medical information 30 from the storage unit 22.

The learning unit 42 performs learning of the learning medical information 30 acquired by the acquisition unit 40 as learning data (also referred to as teacher data) to generate the learned model 38 that outputs information on the presence or absence of the fracture in the growth plate of the subject based on the learning medical information 30. Specifically, the learning unit 42 generates, by machine learning, a plurality of learned models 38 according to combinations of the breeds and the ages that receive the medical image data 32 to which the fracture presence or absence information is added, for each combination of the dog breed represented by the breed information 34 and the age represented by the age information 36, and output the information representing the presence or absence of the fracture in the growth plate in the medical image 33 represented by the medical image data 32.

More specifically, in a case where the medical image data 32A representing the medical image 33A in a non-fractured state among the medical image data 32 to which "Shiba Inu" is added as the dog breed represented by the breed information 34 and "one month" is added as the age represented by the age information 36 is input, the learning unit 42 causes the model to learn such that information (for example, "0") representing that there is no fracture is output. In a case where the medical image data 32B representing the medical image 33B in a fractured state among the medical image data 32 to which "Shiba Inu" is added as the dog breed represented by the breed information 34 and "one month" is added as the age represented by the age information 36 is input, the learning unit 42 causes the model to learn such that information (for example, "1") representing that there is the fracture is output. With the learning, the learned model $38_1$ for which the dog breed is Shiba Inu and the age is one month is generated.

Similarly, in a case where the medical image data 32A representing the medical image 33A in a non-fractured state among the medical image data 32 to which "Shiba Inu" is added as the dog breed represented by the breed information 34 and "two months" is added as the age represented by the age information 36 is input, the learning unit 42 causes the model to learn such that the information representing that there is no fracture is output. In a case where the medical image data 32B representing the medical image 33B in a fractured state among the medical image data 32 to which "Shiba Inu" is added as the dog breed represented by the breed information 34 and "two months" is added as the age represented by the age information 36 is input, the learning unit 42 causes the model to learn such that the information representing that there is the fracture is output. With the learning, the learned model $38_2$ for which the dog breed is Shiba Inu and the age is two months is generated.

Similarly, in a case where the medical image data 32A representing the medical image 33A in a non-fractured state among the medical image data 32 to which "Golden Retriever" is added as the dog breed represented by the breed information 34 and "one month" is added as the age represented by the age information 36 is input, the learning unit 42 causes the model to learn such that the information representing that there is no fracture is output. In a case where the medical image data 32B representing the medical image 33B in a fractured state among the medical image data 32 to which "Golden Retriever" is added as the dog breed represented by the breed information 34 and "one month" is added as the age represented by the age information 36 is input, the learning unit 42 causes the model to learn such that the information representing that there is the fracture is output. With the learning, the learned model $38_4$ for which the dog breed is Golden Retriever and the age is one month is generated.

Figure 7:
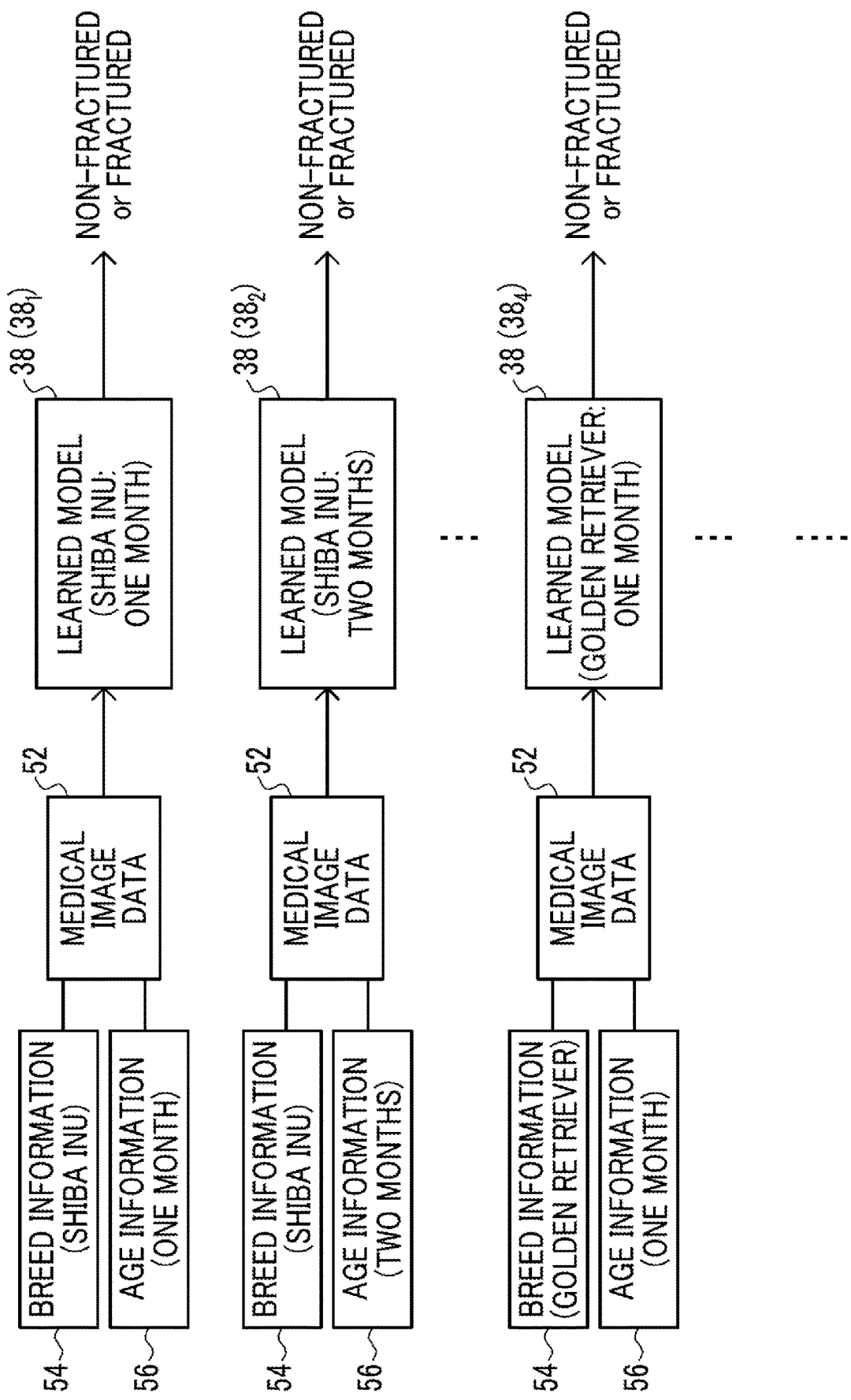
FIG. 7 is a diagram for describing an input and an output of the learned model according to the first embodiment.

For example, an error back propagation method may be employed as an algorithm of the learning by the learning unit 42 described above. As shown in FIG. 7 as an example, the learned model 38 is generated by the learning by the learning unit 42 described above, which receives medical image data 52, breed information 54, and age information 56 for each combination of the breed (dog breed) and the age, and outputs information representing whether there is no fracture or the fracture for the growth plate of the subject appearing in a medical image represented by the input medical image data 52. The learning unit 42 stores the generated learned model 38 in the storage unit 22. In the present embodiment, in a case where the medical image data 52, the breed information 54, and the age information 56 are collectively referred to, the information is referred to as "medical information".

Next, an action of the medical care support device 10 according to the present embodiment in the learning phase will be described with reference to FIG. 8. The CPU 20 executes the learning program 23A to execute learning processing shown in FIG. 8.

Figure 8:
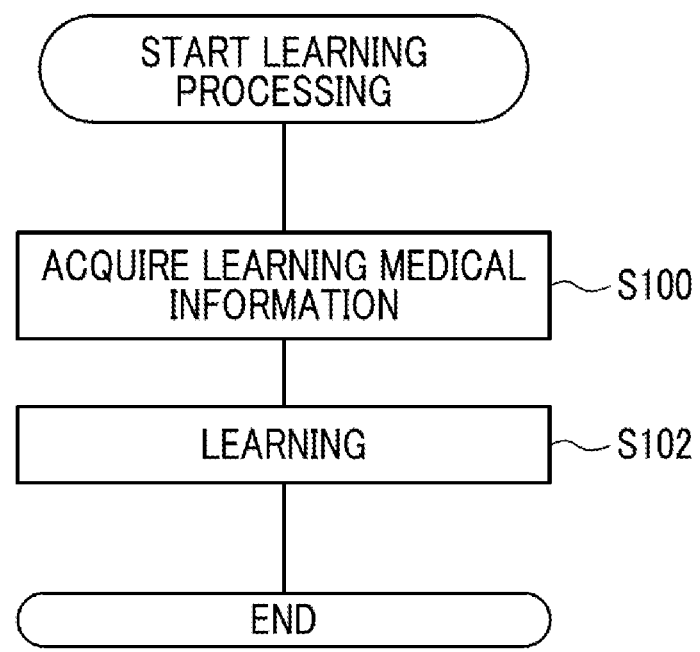
FIG. 8 is a flowchart showing an example of learning processing executed by the medical care support device according to the first embodiment.

In Step S100 in FIG. 8, the acquisition unit 40 acquires the learning medical information 30 from the storage unit 22.

In next Step S102, the learning unit 42 causes the model to learn for each combination of the dog breed and the age with the learning medical information 30 acquired in Step S100 as the learning data, as described above. With the learning, the learning unit 42 generates the learned model 38 that outputs the information on the presence or absence of the fracture in the growth plate of the subject based on the medical image data 52, the breed information 54, and the age information 56. The learning unit 42 stores the generated learned model 38 in the storage unit 22. In a case where the processing in Step S102 ends, the learning processing ends.

Figure 9:
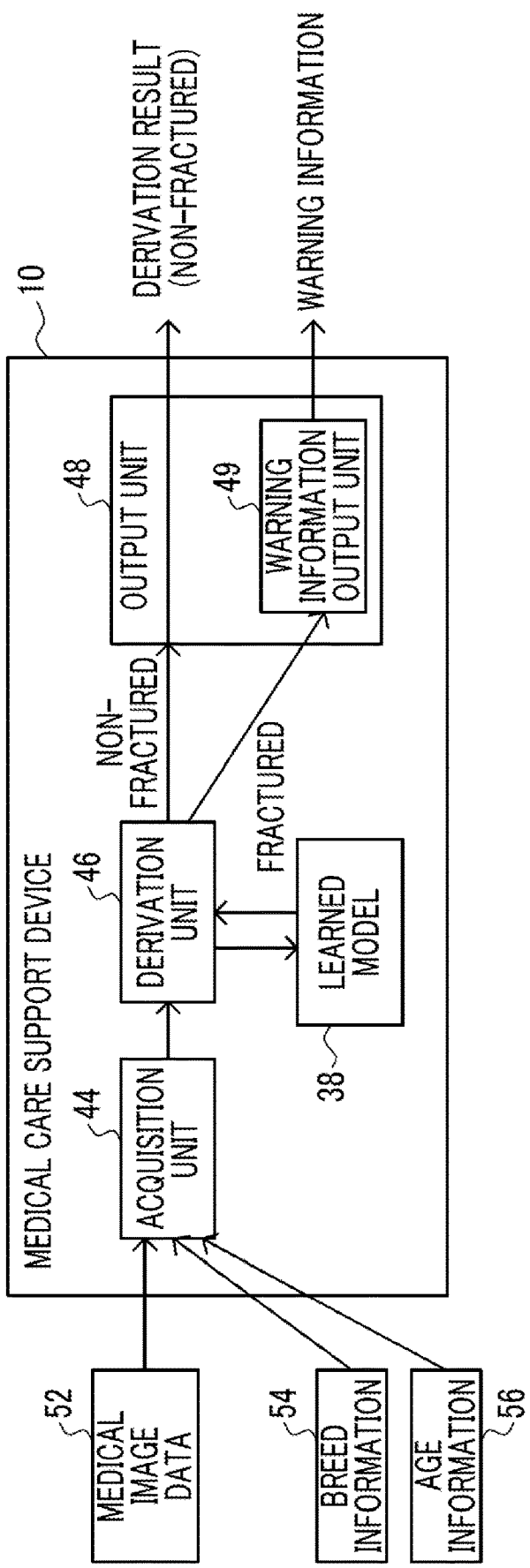
FIG. 9 is a block diagram showing an example of a functional configuration in an operation phase of the medical care support device according to the first embodiment.

Next, a functional configuration of the medical care support device 10 according to the present embodiment in the operation phase will be described with reference to FIG. 9. As shown in FIG. 9, the medical care support device 10 according to the present embodiment includes an acquisition unit 44, a derivation unit 46, and an output unit 48. The CPU 20 executes the medical care support program 23B to function as the acquisition unit 44, the derivation unit 46, and the output unit 48. The acquisition unit 44 is an example of an acquisition unit of the present disclosure, and the derivation unit 46 is an example of a determination unit of the present disclosure. The medical care support device 10 may be the same device in the learning phase and the operation phase or may be different devices.

The acquisition unit 44 acquires the medical image data 52 representing a medical image obtained by imaging an animal of a subject which is a medical care target by the user such as the veterinarian using the medical image capturing device, the breed information 54 representing a dog breed of the subject, and the age information 56 representing an age of the subject as the medical information. Each of the breed information 54 and the age information 56 may be added to the medical image data 52 or may be input by the user through an operation unit (not shown) of the terminal device 12.

The derivation unit 46 derives the presence or absence of the fracture in the growth plate of the subject, based on the medical information (the medical image data 52, the breed information 54, and the age information 56) acquired by the acquisition unit 44 and the learned model 38 learned in advance by the learning medical information 30. Specifically, the derivation unit 46 inputs the medical image data 52 acquired by the acquisition unit 44 to the learned model 38 according to the combination of the dog breed represented by the breed information 54 and the age represented by the age information 56 which are acquired by the acquisition unit 44. The learned model 38 outputs the information representing the presence or absence of the fracture in the growth plate of the subject according to the input medical information.

In a case where the output from the learned model 38 is the information representing that there is no fracture, the derivation unit 46 derives that there is no fracture in the growth plate for the subject corresponding to the medical information acquired by the acquisition unit 44. Specifically, the derivation unit 46 derives that there is no fracture for the growth plate of the bone appearing in the medical image represented by the medical image data 52. On the other hand, in a case where the output from the learned model 38 is the information representing that there is the fracture, the derivation unit 46 derives that there is the fracture in the growth plate for the subject corresponding to the medical information acquired by the acquisition unit 44. Specifically, the derivation unit 46 derives that there is the fracture for the growth plate of the bone appearing in the medical image represented by the medical image data 52.

The output unit 48 includes a warning information output unit 49. The warning information output unit 49 according to the present embodiment is an example of a warning information output unit of the present disclosure. The warning information output unit 49 outputs warning information representing a warning in a case where the growth plate of the subject is fractured. Specifically, in a case where a derivation result by the derivation unit 46 is a derivation result indicating that there is the fracture in the growth plate, the warning information output unit 49 outputs predetermined warning information to the terminal device 12 to display the warning information on a display unit (not shown) of the terminal device 12. The user interprets the medical image represented by the medical image data 52 with reference to the warning information displayed on the display unit of the terminal device 12 and performs the medical care for the fracture in the growth plate of the subject. As described above, in the case where the derivation result by the derivation unit 46 is a derivation result indicating that there is the fracture in the growth plate, the derivation result indicating that there is the fracture in the growth plate may be also displayed on the display unit of the terminal device 12 in addition to the warning information.

In a case where the growth plate of the subject is not fractured, the output unit 48 outputs a derivation result indicating that there is no fracture. Specifically, in a case where the derivation result by the derivation unit 46 is the derivation result indicating that there is no fracture in the growth plate, the output unit 48 outputs the derivation result to the terminal device 12 to display the derivation result on the display unit (not shown) of the terminal device 12. The user performs the medical care for the subject with reference to the derivation result displayed on the display unit of the terminal device 12.

Next, an action of the medical care support device 10 according to the present embodiment in the operation phase will be described with reference to FIG. 10. The CPU 20 executes the medical care support program 23B to execute the medical care support processing shown in FIG. 10.

Figure 10:
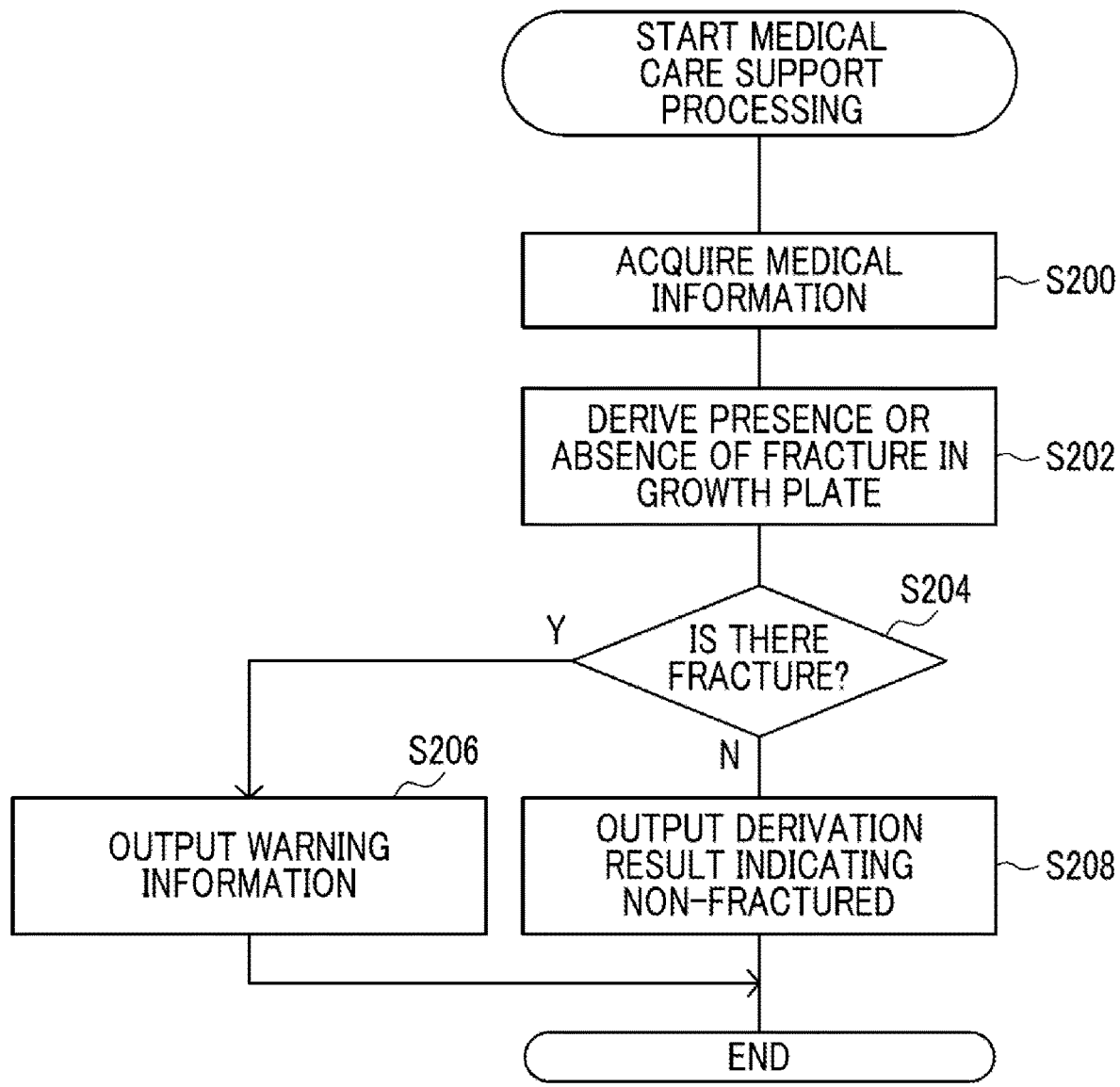
FIG. 10 is a flowchart showing an example of medical care support processing executed by the medical care support device according to the first embodiment.

In Step S200 in FIG. 10, the acquisition unit 44 acquires the medical information of the dog which is the subject and outputs the medical information to the derivation unit 46. Specifically, the acquisition unit 44 acquires the medical image data 52 representing a medical image obtained by imaging a dog of a subject which is the medical care target by the user using the medical image capturing device, the breed information 54 representing a breed of the subject, and the age information 56 representing an age of the subject.

In next Step S202, the derivation unit 46 derives the presence or absence of a fracture in the growth plate of the subject, based on the medical information input from the acquisition unit 44 and the learned model 38, as described above. Specifically, the derivation unit 46 inputs the medical image data 52 to the learned model 38 selected according to the combination of the breed information 54 and the age information 56 in the input medical information to acquire the information representing the presence or absence of the fracture in the growth plate of the subject which is output from the learned model 38.

Figure 11:
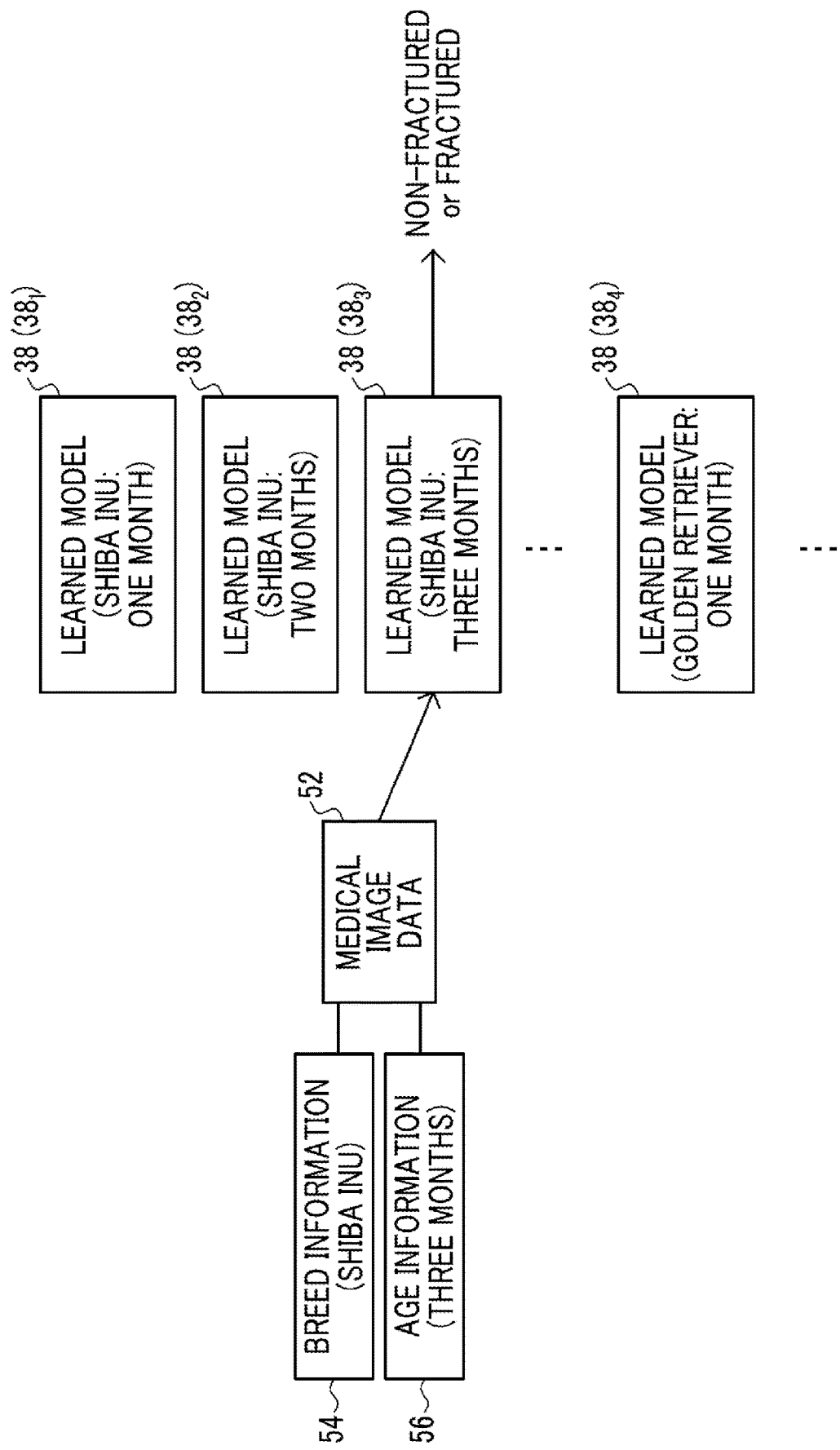
FIG. 11 is a diagram for describing derivation of the presence or absence of a fracture of a growth plate using the learned model according to a combination of a dog breed and an age in the medical care support device according to the first embodiment.

For example, as shown in FIG. 11, in a case where the dog breed represented by the breed information 54 in the medical information is "Shiba Inu" and the information represented by the age information 56 is "three months", the derivation unit 46 inputs the medical image data 52 to the learned model $38_3$ for which the dog breed is Shiba Inu and the age is three months. The information representing the presence or absence of the fracture in the growth plate of the subject is output from the learned model $38_3$.

In next Step S204, the derivation unit 46 determines whether or not there is the fracture in the growth plate of the subject. In a case where the learned model 38 outputs the information representing that there is the fracture in the growth plate of the subject, the determination in Step S204 is affirmative and the processing proceeds to Step S206. In Step S206, the warning information output unit 49 outputs the warning information as described above. In a case where the processing in Step S206 ends, the medical care support processing ends.

On the other hand, in a case where the learned model 38 outputs the information representing that there is no fracture in the growth plate of the subject, the determination in Step S204 is negative and the processing proceeds to Step S208. In Step S208, the output unit 48 outputs the derivation result indicating that there is no fracture as described above. In a case where the processing in Step S208 ends, the medical care support processing ends.

As described above, with the medical care support device 10 according to the present embodiment, the presence or absence of the fracture in the growth plate of the subject is derived based on the medical information including the medical image data 52, the breed information 54, and the age information 56, and the learned model 38. A factor affecting the fracture in the growth plate of the subject includes a breed (dog breed) of the subject. For example, dog breeds such as Pomeranian, Chihuahua, Toy Poodle, and Borzoi are generally known to be prone to fracture, and the growth plates of the dog breeds are also prone to fracture. With the medical care support device 10 according to the present embodiment, the presence or absence of the fracture in the growth plate of the subject is derived using the learned model 38 learned in consideration of the breed (dog breed) which is the factor affecting the fracture in the growth plate. Therefore, it is possible to effectively support the medical care for the fracture in the growth plate using the medical image represented by the medical image data 52.

Second Embodiment

Hereinafter, a second embodiment will be described in detail.

A factor affecting the fracture in the growth plate of the subject includes a thickness of a bone of the subject. In the present embodiment, a form will be described in which the medical care support device 10 supports the medical care for the fracture in the growth plate of the subject using the medical information including the thickness of the bone of the subject.

A configuration of the medical care support system 1 according to the present embodiment is the same as the configuration of the medical care support system 1 according to the first embodiment (refer to FIG. 1), and a description thereof will be omitted.

Figure 12:
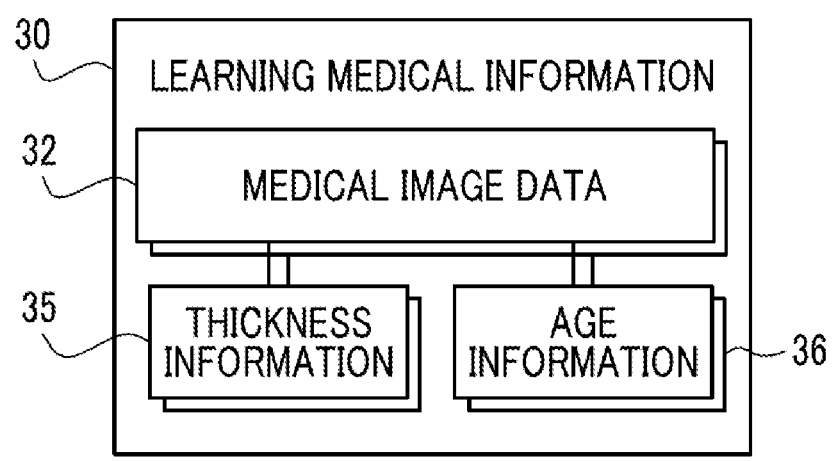
FIG. 12 is a diagram showing an example of learning medical information stored in a storage unit of a medical care support device according to a second embodiment.
Figure 13:
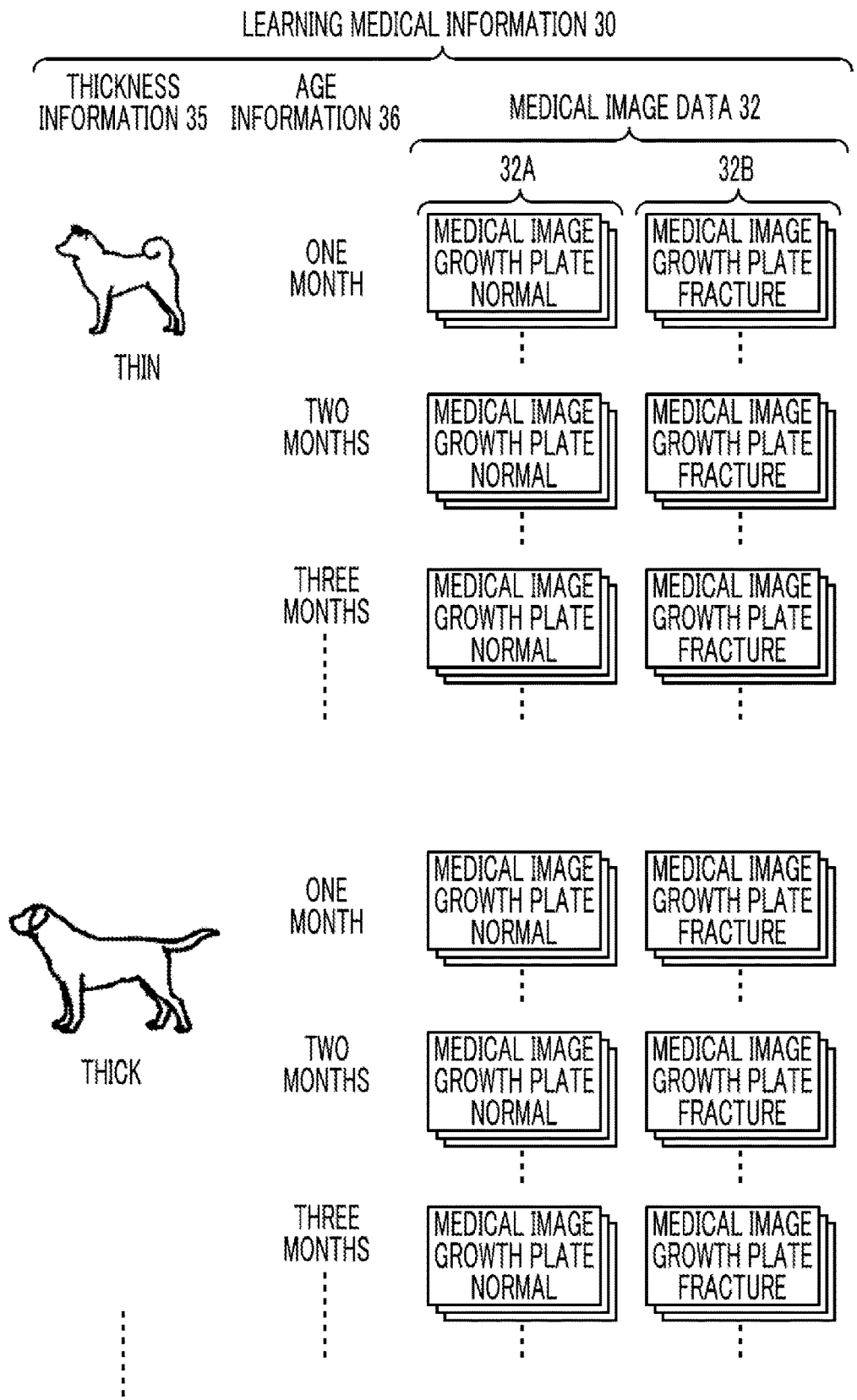
FIG. 13 is a diagram for describing an example of learning medical information according to the second embodiment.

On the other hand, in the medical care support device 10 according to the present embodiment, the contents of the medical information of the subject used for the medical care are different from those of the first embodiment, and the contents of the learning medical information 30 used for learning the learned model 38 are different from those of the first embodiment. Therefore, in the configuration of the medical care support device 10 according to the present embodiment, information included in the learning medical information 30 stored in the storage unit 22 is different from the information (refer to FIGS. 1 and 2) included in the learning medical information 30 stored in the storage unit 22 according to the first embodiment. FIGS. 12 and 13 show an example of the learning medical information 30 according to the present embodiment. As shown in FIGS. 12 and 13, the learning medical information 30 according to the present embodiment includes thickness information 35 instead of the breed information 34 (refer to FIGS. 1 and 2) included in the learning medical information 30 according to the first embodiment.

The thickness information 35 is information representing the thickness of the bone of the subject. Specifically, the thickness information 35 is information representing the thickness of the bone appearing in the medical image data 32 obtained by imaging the subject. As an example, in the present embodiment, the information is information representing the thickness of the bone in two stages and, specifically, is information representing whether the thickness of the bone is thick-boned or thin-boned. The thickness information 35 is not limited to this embodiment and may be information representing the thickness of the bone in three or more stages.

A method of obtaining the thickness information 35 representing the thickness of the bone is not particularly limited. In the present embodiment, the thickness information 35 is obtained from a method other than actually measuring the bone of the subject. For example, a user who interprets the medical image represented by the medical image data 32 or a user who palpates the subject may input the thickness of the bone from an operation unit (not shown) of the terminal device 12. For example, a table representing a correspondence relationship between the dog breed and the thickness of the bone may be prepared in advance, the dog breed of the subject may be acquired from an electronic medical record or the like, and the thickness of the bone corresponding to the acquired dog breed may be acquired from the table prepared in advance. For example, an image of the bone appearing in the medical image 33 may be detected by performing image analysis of the medical image 33 represented by the medical image data 32, and a value derived based on a width of the detected bone and imaging conditions (radiation source, subject, and interval between radiation detectors) may be compared with a predetermined threshold value for determining the thickness of the bone to obtain the thickness of the bone. In this case, the bone whose width is measured may be, for example, set in advance as a bone including the growth plate 60, or an average value of all bones appearing in the medical image 33 may be used.

Figure 14:
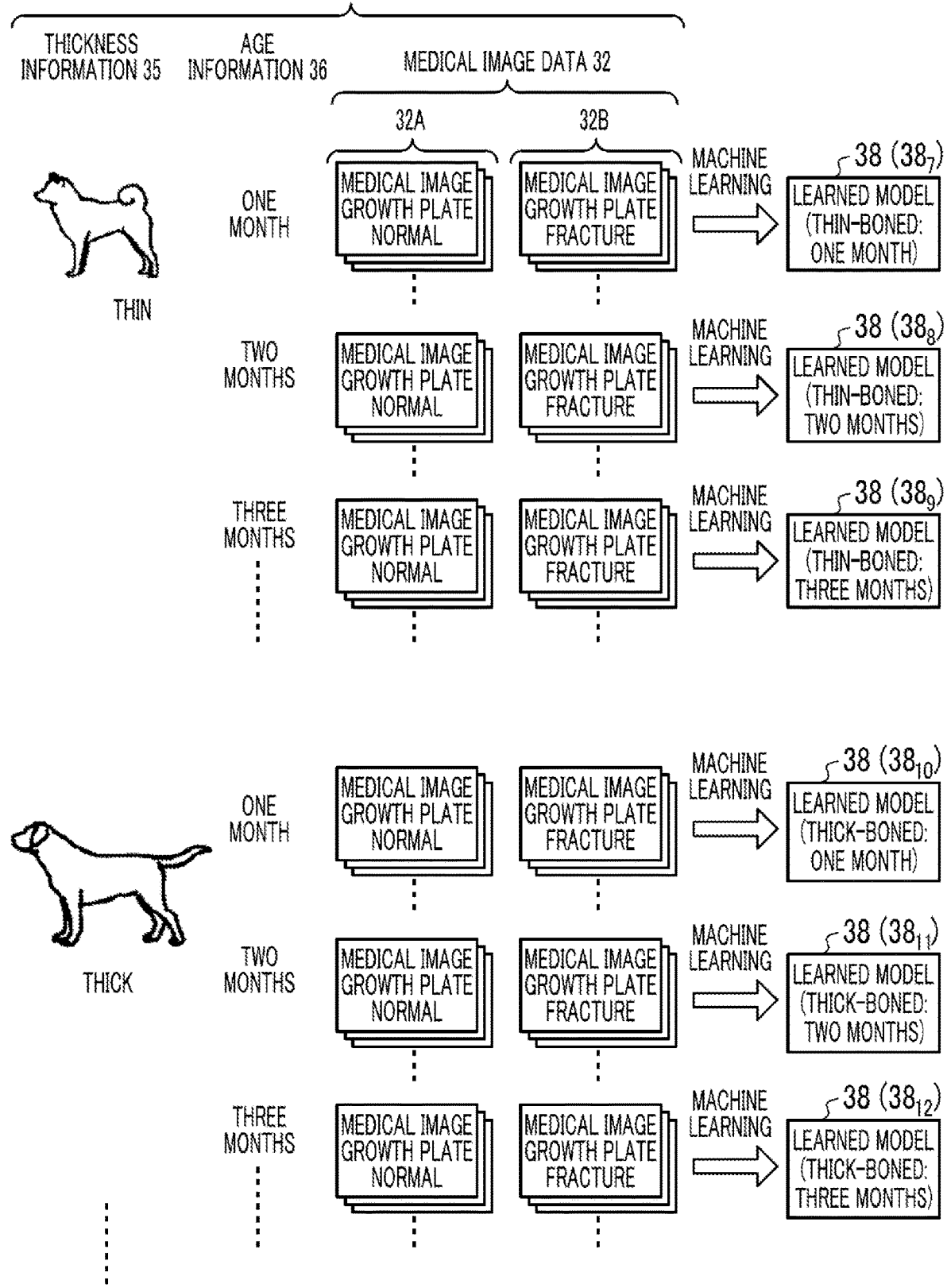
FIG. 14 is a diagram for describing a learned model according to the second embodiment.

As shown in FIG. 14, a learned model 38 according to the present embodiment is generated by machine learning using the learning medical information 30 according to the present embodiment. For example, in a case where the thickness of the bone represented by the thickness information 35 is "thin", a learned model $38_7$ for which the thickness of the bone is thin-boned and the age is one month is generated from the medical image data 32A and 32B whose age represented by the age information 36 is "one month", as shown in FIG. 14. A learned model $38_8$ for which the thickness of the bone is thin-boned and the age is two months is generated from the medical image data 32A and 32B whose age represented by the age information 36 is "two months". A learned model $38_9$ for which the thickness of the bone is thin-boned and the age is three months is generated from the medical image data 32A and 32B whose age represented by the age information 36 is "three months".

For example, in a case where the thickness of the bone represented by the thickness information 35 is "thick", a learned model $38_{10}$ for which the thickness of the bone is thick-boned and the age is one month is generated from the medical image data 32A and 32B whose age represented by the age information 36 is "one month", as shown in FIG. 14. A learned model $38_{11}$ for which the thickness of the bone is thick-boned and the age is two months is generated from the medical image data 32A and 32B whose age represented by the age information 36 is "two months". A learned model $38_{12}$ for which the thickness of the bone is thick-boned and the age is three months is generated from the medical image data 32A and 32B whose age represented by the age information 36 is "three months". As described above, an example of the learned model 38 includes a neural network model.

Although FIG. 14 shows the six learned models $38_7$ to $38_{12}$, the number of learned models 38 to be generated is not limited to six. In a case where the learned models $38_7$ to $38_{12}$ are collectively referred to without distinction, the symbols "7" to "12" for distinguishing the individual models are omitted and the models are referred to as "learned model 38".

Next, a functional configuration of the medical care support device 10 according to the present embodiment in the learning phase will be described. The overall configuration of the medical care support device 10 according to the present embodiment in the learning phase is the same as that of the medical care support device 10 according to the first embodiment (refer to FIG. 6). On the other hand, there is a difference in a specific operation of the learning unit 42 in the medical care support device 10 according to the present embodiment for generating the learned model 38 based on the learning medical information 30. Therefore, the specific operation of the learning unit 42 will be described.

The learning unit 42 according to the present embodiment generates, by machine learning, a plurality of learned models 38 according to combinations of the thicknesses of the bone and the ages that receive the medical image data 32 to which the fracture presence or absence information is added, for each combination of the thickness of the bone represented by the thickness information 35 and the age represented by the age information 36, and output the information representing the presence or absence of the fracture in the growth plate in the medical image 33 represented by the medical image data 32.

More specifically, in a case where the medical image data 32A representing the medical image 33A in a non-fractured state among the medical image data 32 to which "thin-boned" is added as the thickness of the bone represented by the thickness information 35 and "one month" is added as the age represented by the age information 36 is input, the learning unit 42 causes the model to learn such that information (for example, "0") representing that there is no fracture is output. In a case where the medical image data 32B representing the medical image 33B in a fractured state among the medical image data 32 to which "thin-boned" is added as the thickness of the bone represented by the thickness information 35 and "one month" is added as the age represented by the age information 36 is input, the learning unit 42 causes the model to learn such that information (for example, "1") representing that there is the fracture is output. With the learning, the learned model $38_7$ for which the thickness of the bone is thin-boned and the age is one month is generated.

Similarly, in a case where the medical image data 32A representing the medical image 33A in a non-fractured state among the medical image data 32 to which "thin-boned" is added as the thickness of the bone represented by the thickness information 35 and "two months" is added as the age represented by the age information 36 is input, the learning unit 42 causes the model to learn such that the information representing that there is no fracture is output. In a case where the medical image data 32B representing the medical image 33B in a fractured state among the medical image data 32 to which "thin-boned" is added as the thickness of the bone represented by the thickness information 35 and "two months" is added as the age represented by the age information 36 is input, the learning unit 42 causes the model to learn such that the information representing that there is the fracture is output. With the learning, the learned model $38_8$ for which the thickness of the bone is thin-boned and the age is two months is generated.

Similarly, in a case where the medical image data 32A representing the medical image 33A in a non-fractured state among the medical image data 32 to which "thick-boned" is added as the thickness of the bone represented by the thickness information 35 and "one month" is added as the age represented by the age information 36 is input, the learning unit 42 causes the model to learn such that the information representing that there is no fracture is output. In a case where the medical image data 32B representing the medical image 33B in a fractured state among the medical image data 32 to which "thick-boned" is added as the thickness of the bone represented by the thickness information 35 and "one month" is added as the age represented by the age information 36 is input, the learning unit 42 causes the model to learn such that the information representing that there is the fracture is output. With the learning, the learned model $38_{10}$ for which the thickness of the bone is thick-boned and the age is one month is generated.

Figure 15:
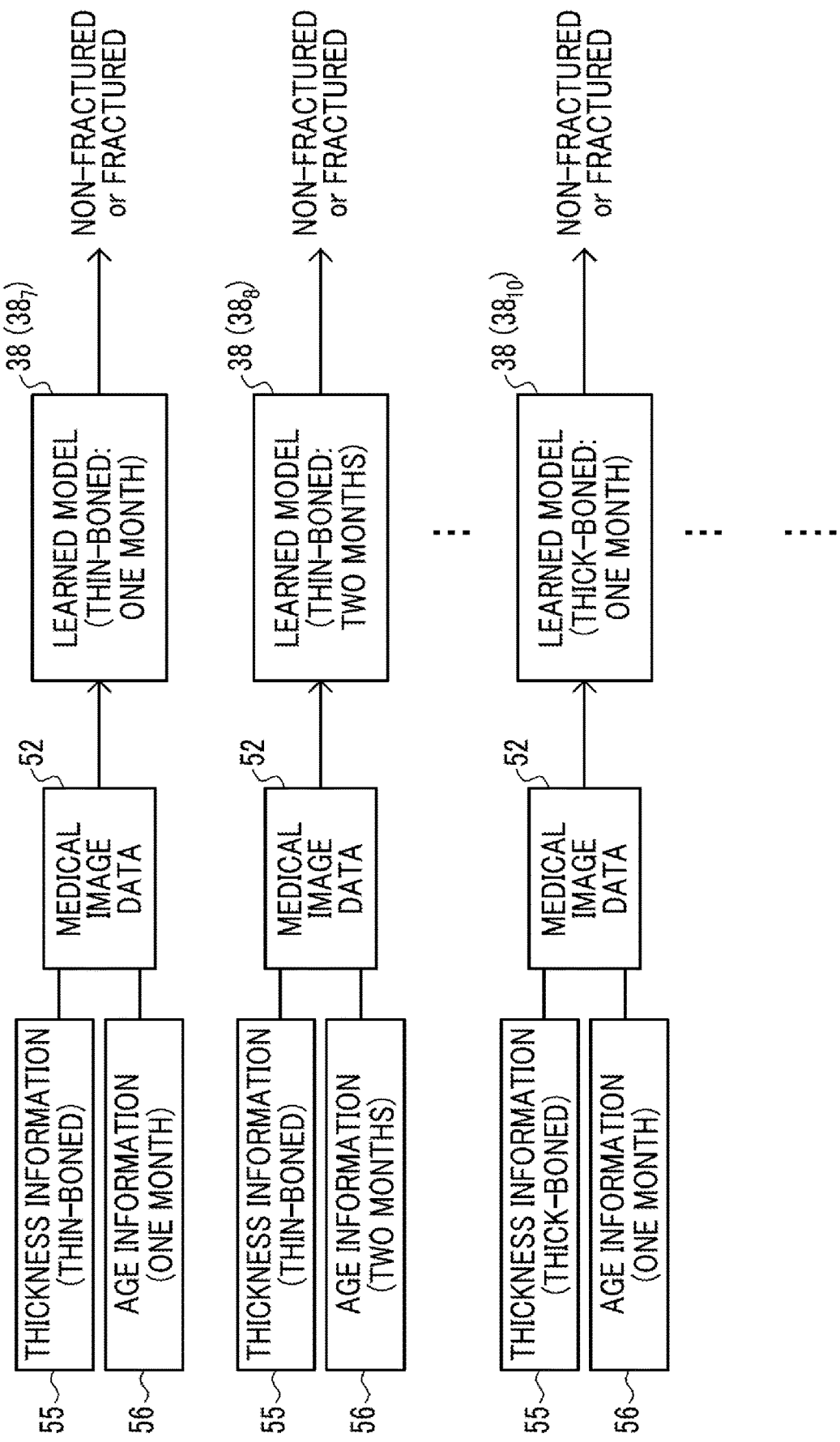
FIG. 15 is a diagram for describing an input and an output of the learned model according to the second embodiment.

For example, as described above, the error back propagation method may be employed as an algorithm of the learning by the learning unit 42 described above. As shown in FIG. 15 as an example, the learned model 38 is generated by the learning by the learning unit 42 described above, which receives the medical image data 52, the thickness information 55, and the age information 56 for each combination of the thickness of the bone and the age, and outputs information representing whether there is no fracture or the fracture for the growth plate of the subject appearing in the medical image represented by the input medical image data 52. The learning unit 42 stores the generated learned model 38 in the storage unit 22.

An action of the medical care support device 10 according to the present embodiment in the learning phase, that is, the learning processing executed by the medical care support device 10 is the same as the learning processing (refer to FIG. 8) executed by the medical care support device 10 according to the first embodiment, and thus the description thereof is omitted.

Figure 16:
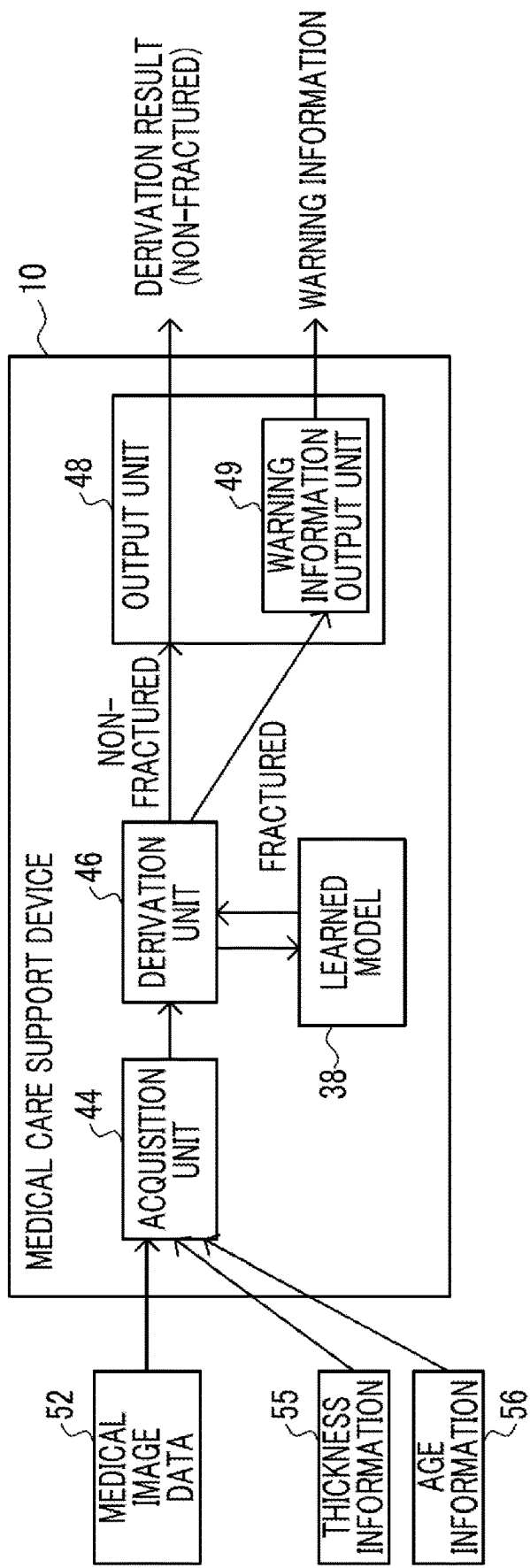
FIG. 16 is a block diagram showing an example of a functional configuration in an operation phase of the medical care support device according to the second embodiment.

Next, a functional configuration of the medical care support device 10 according to the present embodiment in the operation phase will be described with reference to FIG. 16. The overall configuration of the medical care support device 10 according to the present embodiment in the operation phase is the same as that of the medical care support device 10 according to the first embodiment (refer to FIG. 9). Specific operations of the acquisition unit 44 and the derivation unit 46 in the medical care support device 10 according to the present embodiment are different. Therefore, the specific operations of the acquisition unit 44 and the derivation unit 46 will be described.

The acquisition unit 44 acquires the medical image data 52 representing a medical image obtained by imaging the subject, the thickness information 55 representing the thickness of the bone of the subject, and the age information 56 representing the age of the subject as the medical information. Each of the thickness information 55 and the age information 56 may be added to the medical image data 52 or may be input by the user through an operation unit (not shown) of the terminal device 12.

The derivation unit 46 derives the presence or absence of the fracture in the growth plate of the subject, based on the medical information (the medical image data 52, the thickness information 55, and the age information 56) acquired by the acquisition unit 44 and the learned model 38 learned in advance by the learning medical information 30. Specifically, the derivation unit 46 inputs the medical image data 52 acquired by the acquisition unit 44 to the learned model 38 according to the combination of the thickness of the bone represented by the thickness information 55 and the age represented by the age information 56 which are acquired by the acquisition unit 44. The learned model 38 outputs the information representing the presence or absence of the fracture in the growth plate of the subject according to the input medical information.

Next, an action of the medical care support device 10 according to the present embodiment in the operation phase will be described. The overall flow of the medical care support processing is the same as the medical care support processing shown in FIG. 10 according to the first embodiment and thus will be described with reference to FIG. 10.

In Step S200, the acquisition unit 44 acquires the medical information of the dog which is the subject and outputs the medical information to the derivation unit 46. Specifically, the acquisition unit 44 acquires the medical image data 52 representing the medical image obtained by imaging the dog of the subject which is the medical care target by the user using the medical image capturing device, the thickness information 55 representing the thickness of the bone of the subject, and the age information 56 representing the age of the subject.

In next Step S202, the derivation unit 46 derives the presence or absence of a fracture in the growth plate of the subject, based on the medical information input from the acquisition unit 44 and the learned model 38, as described above. Specifically, the derivation unit 46 inputs the medical image data 52 to the learned model 38 selected according to the combination of the thickness information 55 and the age information 56 in the input medical information to acquire the information representing the presence or absence of the fracture in the growth plate of the subject which is output from the learned model 38.

Figure 17:
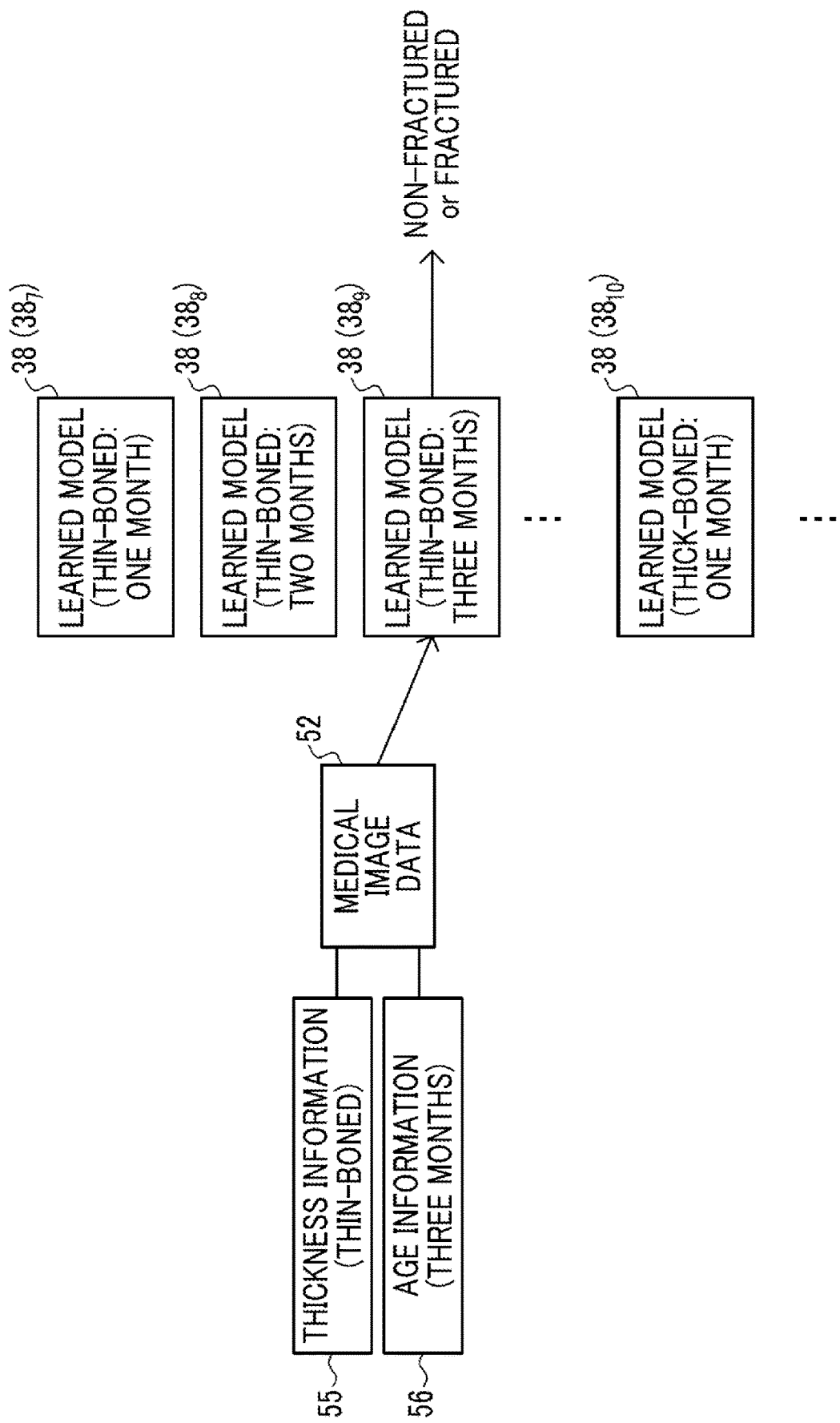
FIG. 17 is a diagram for describing derivation of the presence or absence of a fracture of a growth plate using the learned model according to a combination of a bone thickness and an age in the medical care support device according to the second embodiment.

For example, as shown in FIG. 17, in a case where the thickness of the bone represented by the thickness information 55 in the medical information is "thin-boned" and the information represented by the age information 56 is "three months", the derivation unit 46 inputs the medical image data 52 to the learned model $38_9$ for which the thickness of the bone is thin-boned and the age is three months. The information representing the presence or absence of the fracture in the growth plate of the subject is output from the learned model $38_9$.

In next Step S204, the derivation unit 46 determines whether or not there is the fracture in the growth plate of the subject as described above. The determination in Step S204 is affirmative in a case where the learned model 38 outputs the information representing that there is the fracture in the growth plate of the subject, the warning information output unit 49 outputs the warning information as described above in next Step S206, and then the medical care support processing ends.

On the other hand, the determination in Step S204 is negative in a case where the learned model 38 outputs the information representing that there is no fracture in the growth plate of the subject, the output unit 48 outputs the derivation result indicating that there is no fracture as described above in next Step S208, and then the medical care support processing ends.

As described above, with the medical care support device 10 according to the present embodiment, the presence or absence of the fracture in the growth plate of the subject is derived based on the medical information including the medical image data 52, the thickness information 55, and the age information 56, and the learned model 38. A factor affecting the fracture in the growth plate of the subject includes the thickness of the bone, particularly the thickness of the bone having the growth plate. For example, there is a known tendency that the thin bone is relatively easily fractured and the growth plate thereof is also easily fractured as compared with the thick bone. With the medical care support device 10 according to the present embodiment, the presence or absence of the fracture in the growth plate of the subject is derived using the learned model 38 learned in consideration of the thickness of the bone which is the factor affecting the fracture in the growth plate. Therefore, it is possible to effectively support the medical care for the fracture in the growth plate using the medical image represented by the medical image data 52.

With the medical care support device 10 according to the present embodiment, even in a case where the subject is a hybrid such as a so-called mixed dog or in a case where the dog breed is unknown, it is possible to derive the presence or absence of the fracture in the growth plate of the subject in consideration of the thickness of the bone and thus to more effectively support the medical care.

Third Embodiment

Hereinafter, the third embodiment will be described in detail.

A factor affecting the fracture in the growth plate of the subject includes a body type of the subject. In the present embodiment, a form will be described in which the medical care support device 10 supports the medical care for the fracture in the growth plate of the subject using the medical information including the body type of the subject.

A configuration of the medical care support system 1 according to the present embodiment is the same as the configuration of the medical care support system 1 according to the first embodiment (refer to FIG. 1), and a description thereof will be omitted.

Figure 18:
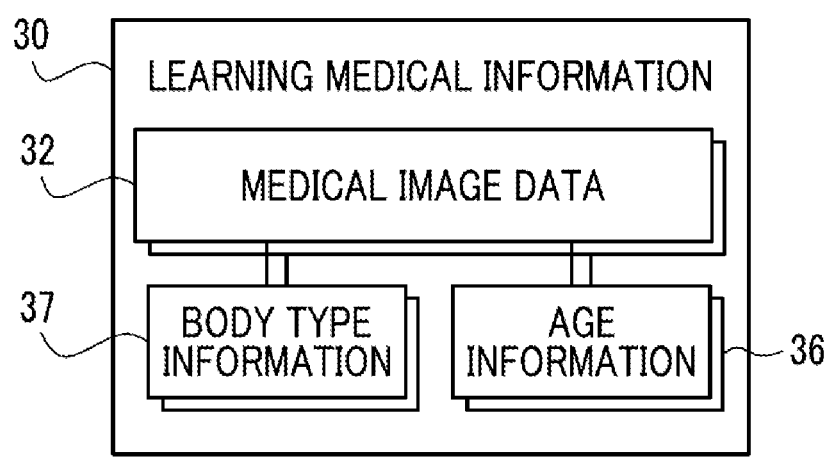
FIG. 18 is a diagram showing an example of learning medical information stored in a storage unit of a medical care support device according to a third embodiment.
Figure 19:
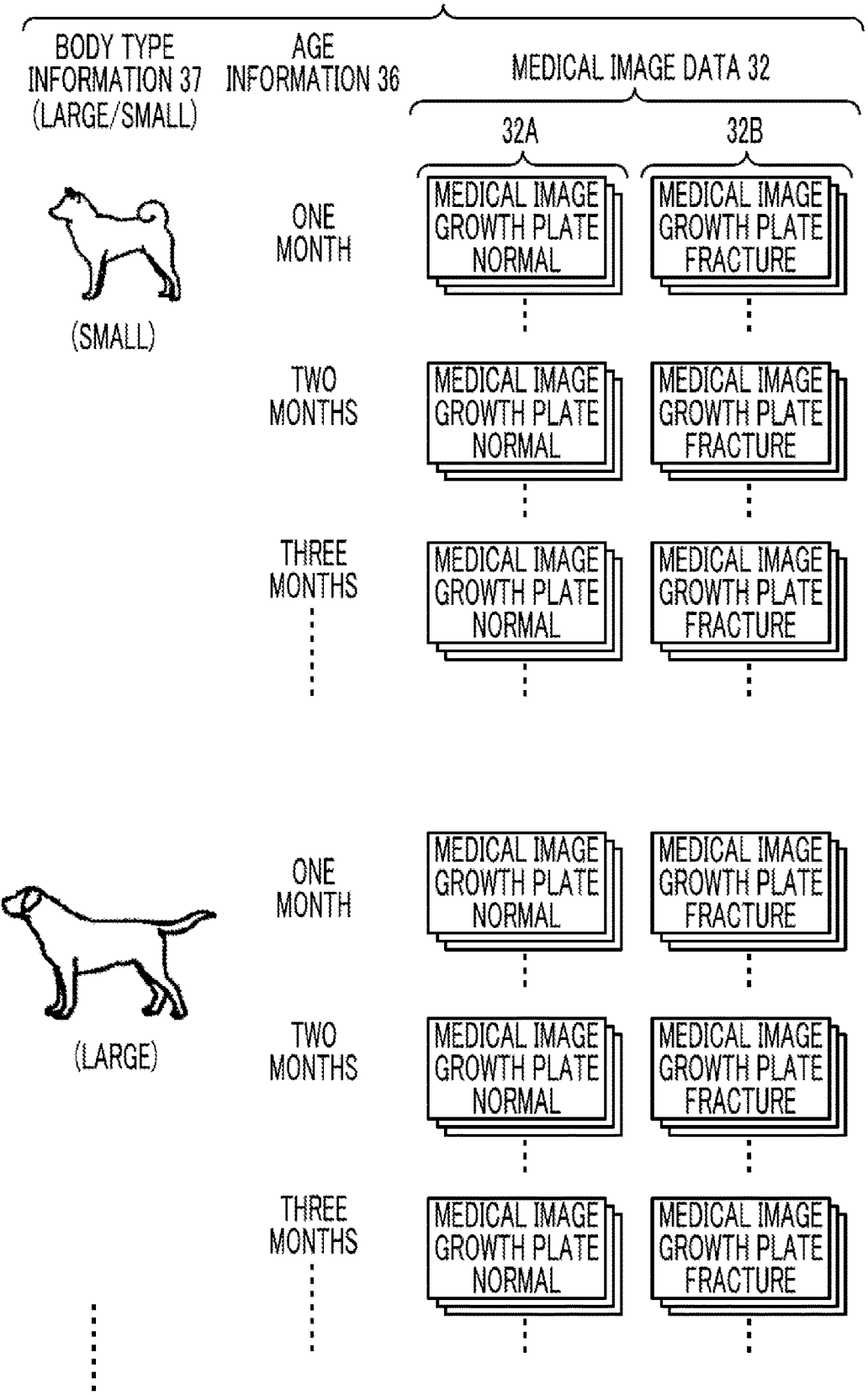
FIG. 19 is a diagram for describing an example of the learning medical information according to the third embodiment.

On the other hand, in the medical care support device 10 according to the present embodiment, the contents of the medical information of the subject used for the medical care are different from those of the first embodiment, and the contents of the learning medical information 30 used for learning the learned model 38 are different from those of the first embodiment. Therefore, in the configuration of the medical care support device 10 according to the present embodiment, information included in the learning medical information 30 stored in the storage unit 22 is different from the information (refer to FIGS. 1 and 2) included in the learning medical information 30 stored in the storage unit 22 according to the first embodiment. FIGS. 18 and 19 show an example of the learning medical information 30 according to the present embodiment. As shown in FIGS. 18 and 19, the learning medical information 30 according to the present embodiment includes body type information 37 instead of the breed information 34 (refer to FIGS. 1 and 2) included in the learning medical information 30 according to the first embodiment.

The body type information 37 is information representing the body type of the subject. Specifically, the body type information 37 is information representing a size of the body of the subject. As an example, in the present embodiment, the information is information representing the size of the body of the subject in two stages and, specifically, is information representing whether the body type is small or large. The body type information 37 is not limited to this embodiment and may be information representing the size of the body in three or more stages such as small, medium, and large. The body type information 37 is not limited to the information representing a so-called small dog or large dog as in the present embodiment and may be, for example, information representing the body type such as obesity type or lean type.

A method of obtaining the body type information 37 is not particularly limited. For example, the user who interprets the medical image represented by the medical image data 32 may input the body type from an operation unit (not shown) of the terminal device 12. Also, for example, a table representing a correspondence relationship between the dog breed and the body type may be prepared in advance, the dog breed of the subject may be acquired from an electronic medical record or the like, and the body type corresponding to the acquired dog breed may be acquired from the table prepared in advance. For example, the body type of the subject may be automatically acquired from a comparison result of comparing sizes of an examination table and the subject based on a captured image obtained by imaging the subject on the examination table with a camera or the like.

Figure 20:
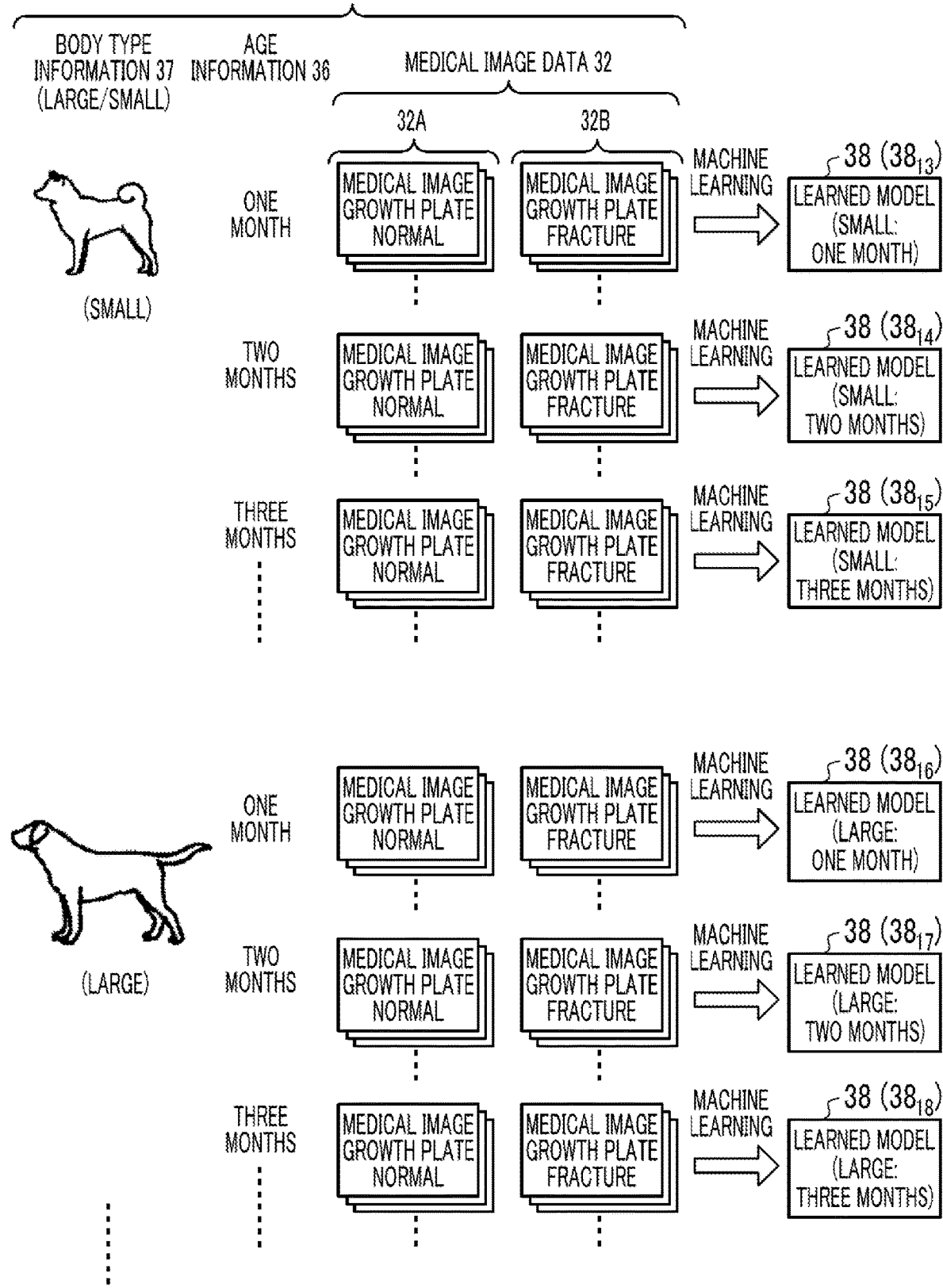
FIG. 20 is a diagram for describing a learned model according to the third embodiment.

As shown in FIG. 20, the learned model 38 according to the present embodiment is generated by machine learning using the learning medical information 30 according to the present embodiment. For example, in a case where the body type represented by the body type information 37 is "small", a learned model $38_{13}$ for which the body type is small and the age is one month is generated from the medical image data 32A and 32B whose age represented by the age information 36 is "one month", as shown in FIG. 20. A learned model $38_{14}$ for which the body type is small and the age is two months is generated from the medical image data 32A and 32B whose age represented by the age information 36 is "two months". A learned model $38_{15}$ for which the body type is small and the age is three months is generated from the medical image data 32A and 32B whose age represented by the age information 36 is "three months".

For example, in a case where the body type represented by the body type information 37 is "large", a learned model $38_{16}$ for which the body type is large and the age is one month is generated from the medical image data 32A and 32B whose age represented by the age information 36 is "one month", as shown in FIG. 20. A learned model $38_{17}$ for which the body type is large and the age is two months is generated from the medical image data 32A and 32B whose age represented by the age information 36 is "two months". A learned model $38_{18}$ for which the body type is large and the age is three months is generated from the medical image data 32A and 32B whose age represented by the age information 36 is "three months". As described above, an example of the learned model 38 includes a neural network model.

Although FIG. 20 shows the six learned models $38_{13}$ to $38_{18}$, the number of learned models 38 to be generated is not limited to six. In a case where the learned models $38_{13}$ to $38_{18}$ are collectively referred to without distinction, the symbols "13" to "18" for distinguishing the individual models are omitted and the models are referred to as "learned model 38".

Next, a functional configuration of the medical care support device 10 according to the present embodiment in the learning phase will be described. The overall configuration of the medical care support device 10 according to the present embodiment in the learning phase is the same as that of the medical care support device 10 according to the first embodiment (refer to FIG. 6). On the other hand, there is a difference in a specific operation of the learning unit 42 in the medical care support device 10 according to the present embodiment for generating the learned model 38 based on the learning medical information 30. Therefore, the specific operation of the learning unit 42 will be described.

The learning unit 42 according to the present embodiment generates, by machine learning, a plurality of learned models 38 according to combinations of the body types of the subject and the ages that receive the medical image data 32 to which the fracture presence or absence information is added, for each combination of the body type of the subject represented by the body type information 37 and the age represented by the age information 36, and output the information representing the presence or absence of the fracture in the growth plate in the medical image 33 represented by the medical image data 32.

More specifically, in a case where the medical image data 32A representing the medical image 33A in a non-fractured state among the medical image data 32 to which "small" is added as the body type represented by the body type information 37 and "one month" is added as the age represented by the age information 36 is input, the learning unit 42 causes the model to learn such that information (for example, "0") representing that there is no fracture is output. In a case where the medical image data 32B representing the medical image 33B in a fractured state among the medical image data 32 to which "small" is added as the body type represented by the body type information 37 and "one month" is added as the age represented by the age information 36 is input, the learning unit 42 causes the model to learn such that information (for example, "1") representing that there is the fracture is output. With the learning, the learned model $38_{13}$ for which the body type is small and the age is one month is generated.

Similarly, in a case where the medical image data 32A representing the medical image 33A in a non-fractured state among the medical image data 32 to which "small" is added as the body type represented by the body type information 37 and "two months" is added as the age represented by the age information 36 is input, the learning unit 42 causes the model to learn such that the information representing that there is no fracture is output. In a case where the medical image data 32B representing the medical image 33B in a fractured state among the medical image data 32 to which "small" is added as the body type represented by the body type information 37 and "two months" is added as the age represented by the age information 36 is input, the learning unit 42 causes the model to learn such that the information representing that there is the fracture is output. With the learning, the learned model $38_{14}$ for which the body type is small and the age is two months is generated.

Similarly, in a case where the medical image data 32A representing the medical image 33A in a non-fractured state among the medical image data 32 to which "large" is added as the body type represented by the body type information 37 and "one month" is added as the age represented by the age information 36 is input, the learning unit 42 causes the model to learn such that the information representing that there is no fracture is output. In a case where the medical image data 32B representing the medical image 33B in a fractured state among the medical image data 32 to which "large" is added as the body type represented by the body type information 37 and "one month" is added as the age represented by the age information 36 is input, the learning unit 42 causes the model to learn such that the information representing that there is the fracture is output. With the learning, the learned model $38_{16}$ for which the body type is large and the age is one month is generated.

Figure 21:
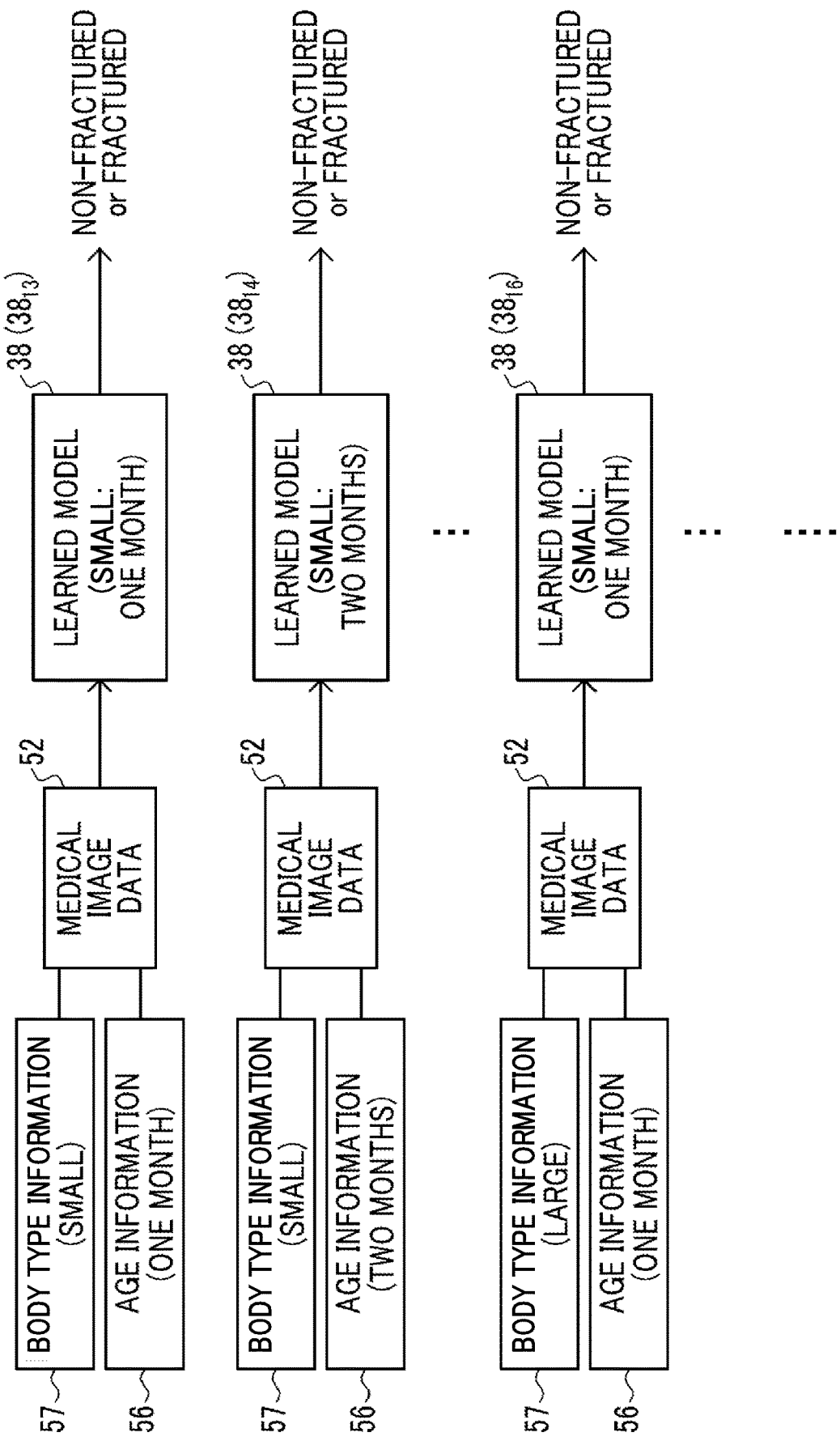
FIG. 21 is a diagram for describing an input and an output of the learned model according to the third embodiment.

For example, as described above, the error back propagation method may be employed as an algorithm of the learning by the learning unit 42 described above. As shown in FIG. 21 as an example, the learned model 38 is generated by the learning by the learning unit 42 described above, which receives the medical image data 52, the body type information 57, and the age information 56 for each combination of the body type and the age, and outputs information representing whether there is no fracture or the fracture for the growth plate of the subject appearing in the medical image represented by the input medical image data 52. The learning unit 42 stores the generated learned model 38 in the storage unit 22.

An action of the medical care support device 10 according to the present embodiment in the learning phase, that is, the learning processing executed by the medical care support device 10 is the same as the learning processing (refer to FIG. 8) executed by the medical care support device 10 according to the first embodiment, and thus the description thereof is omitted.

Figure 22:
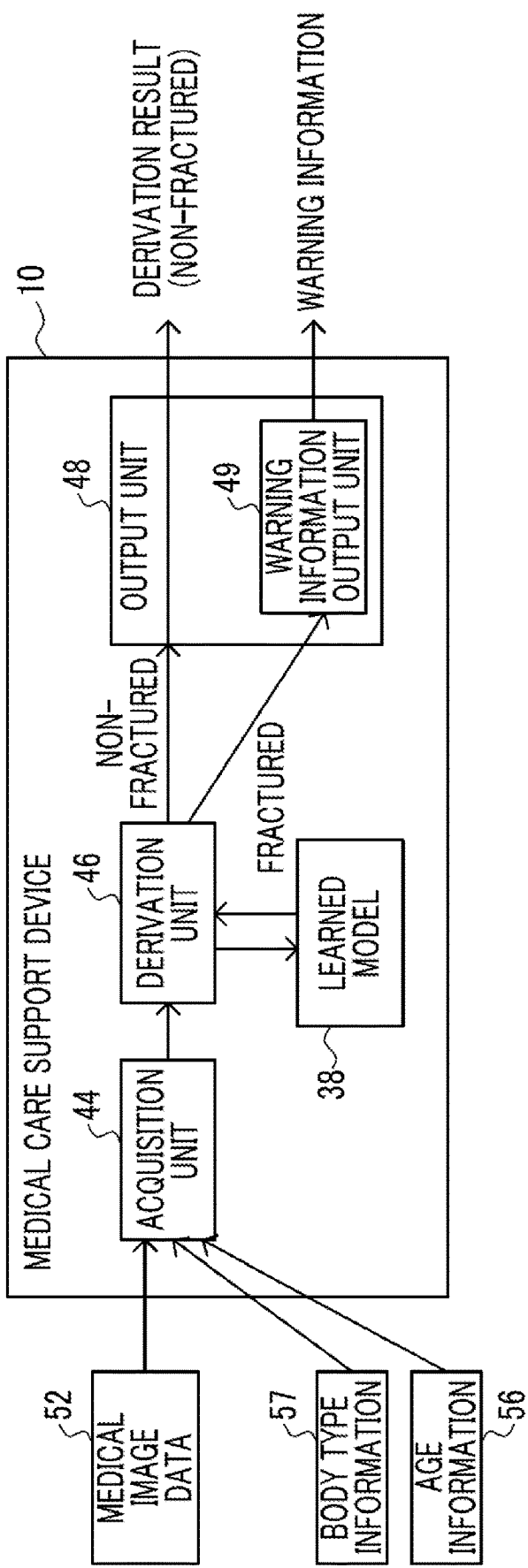
FIG. 22 is a block diagram showing an example of a functional configuration in an operation phase of the medical care support device according to the third embodiment.

Next, a functional configuration of the medical care support device 10 according to the present embodiment in the operation phase will be described with reference to FIG. 22. The overall configuration of the medical care support device 10 according to the present embodiment in the operation phase is the same as that of the medical care support device 10 according to the first embodiment (refer to FIG. 9). Specific operations of the acquisition unit 44 and the derivation unit 46 in the medical care support device 10 according to the present embodiment are different. Therefore, the specific operations of the acquisition unit 44 and the derivation unit 46 will be described.

The acquisition unit 44 acquires the medical image data 52 representing the medical image obtained by imaging the subject, the body type information 57 representing the body type of the subject, and the age information 56 representing the age of the subject as the medical information. Each of the body type information 57 and the age information 56 may be added to the medical image data 52 or may be input by the user through an operation unit (not shown) of the terminal device 12.

The derivation unit 46 derives the presence or absence of the fracture in the growth plate of the subject, based on the medical information (the medical image data 52, the body type information 57, and the age information 56) acquired by the acquisition unit 44 and the learned model 38 learned in advance by the learning medical information 30. Specifically, the derivation unit 46 inputs the medical image data 52 acquired by the acquisition unit 44 to the learned model 38 according to the combination of the body type represented by the body type information 57 and the age represented by the age information 56 which are acquired by the acquisition unit 44. The learned model 38 outputs the information representing the presence or absence of the fracture in the growth plate of the subject according to the input medical information.

Next, an action of the medical care support device 10 according to the present embodiment in the operation phase will be described. The overall flow of the medical care support processing is the same as the medical care support processing shown in FIG. 10 according to the first embodiment and thus will be described with reference to FIG. 10.

In Step S200, the acquisition unit 44 acquires the medical information of the dog which is the subject and outputs the medical information to the derivation unit 46. Specifically, the acquisition unit 44 acquires the medical image data 52 representing the medical image obtained by imaging the dog of the subject which is the medical care target by the user using the medical image capturing device, the body type information 57 representing the body type of the subject, and the age information 56 representing the age of the subject.

In next Step S202, the derivation unit 46 derives the presence or absence of a fracture in the growth plate of the subject, based on the medical information input from the acquisition unit 44 and the learned model 38, as described above. Specifically, the derivation unit 46 inputs the medical image data 52 to the learned model 38 selected according to the combination of the body type information 57 and the age information 56 in the input medical information to acquire the information representing the presence or absence of the fracture in the growth plate of the subject which is output from the learned model 38.

Figure 23:
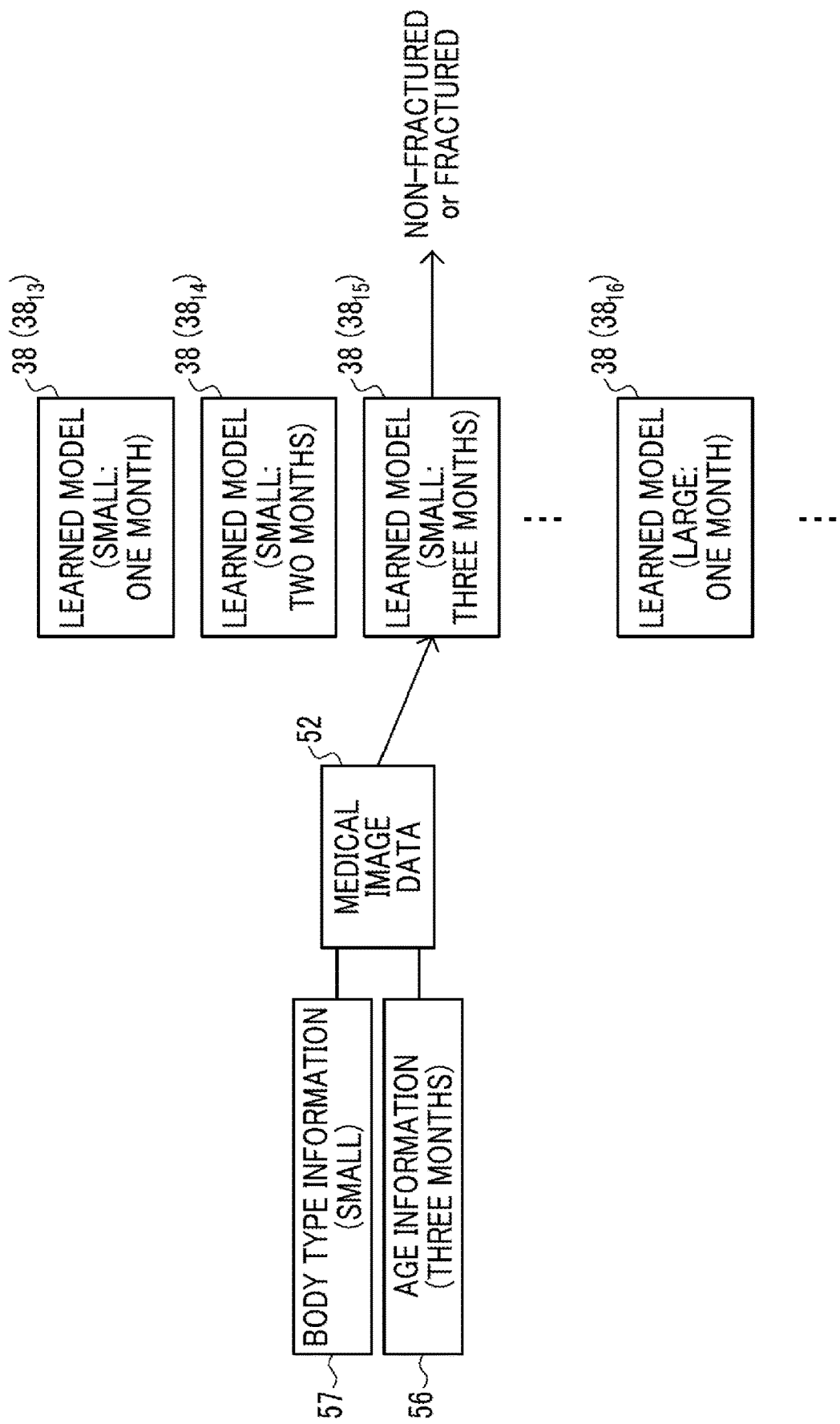
FIG. 23 is a diagram for describing derivation of the presence or absence of a fracture of a growth plate using the learned model according to a combination of a body type and an age in the medical care support device of the third embodiment.

For example, as shown in FIG. 23, in a case where the body type represented by the body type information 57 in the medical information is "small" and the information represented by the age information 56 is "three months", the derivation unit 46 inputs the medical image data 52 to the learned model $38_{15}$ for which the body type is small and the age is three months. The information representing the presence or absence of the fracture in the growth plate of the subject is output from the learned model $38_{15}$.

In next Step S204, the derivation unit 46 determines whether or not there is the fracture in the growth plate of the subject as described above. The determination in Step S204 is affirmative in a case where the learned model 38 outputs the information representing that there is the fracture in the growth plate of the subject, the warning information output unit 49 outputs the warning information as described above in next Step S206, and then the medical care support processing ends.

On the other hand, the determination in Step S204 is negative in a case where the learned model 38 outputs the information representing that there is no fracture in the growth plate of the subject, the output unit 48 outputs the derivation result indicating that there is no fracture as described above in next Step S208, and then the medical care support processing ends.

As described above, with the medical care support device 10 according to the present embodiment, the presence or absence of the fracture in the growth plate of the subject is derived based on the medical information including the medical image data 52, the body type information 57, and the age information 56, and the learned model 38. A factor affecting the fracture in the growth plate of the subject includes the body type of the subject. For example, there is a known tendency that the small dog is relatively easily fractured and the growth plate thereof is also easily fractured as compared with the large dog. In other words, the growth plate tends to be easily fractured as the body type becomes smaller. For example, there is a known tendency that a dog having a delicate body type is relatively easily fractured and the growth plate thereof is also easily fractured as compared with a dog having a sturdy body type. In other words, the growth plate tends to be easily fractured as the body type becomes more delicate. For example, there is a known tendency that a lean type dog or an obesity type dog is relatively easily fractured and the growth plate thereof is also easily fractured as compared with a dog having a standard body type. In other words, the growth plate tends to be easily fractured as the body type deviates more from the standard body type. For example, there is a known tendency that a dog having a high body fat percentage is relatively easily fractured and the growth plate thereof is also easily fractured as compared with a dog having a low body fat percentage.

With the medical care support device 10 according to the present embodiment, the presence or absence of the fracture in the growth plate of the subject is derived using the learned model 38 learned in consideration of the body type of the subject which is the factor affecting the fracture in the growth plate. Therefore, it is possible to effectively support the medical care for the fracture in the growth plate using the medical image represented by the medical image data 52.

With the medical care support device 10 according to the present embodiment, even in a case where the subject is a hybrid such as a so-called mixed dog or in a case where the dog breed is unknown, it is possible to derive the presence or absence of the fracture in the growth plate of the subject in consideration of the body type of the subject and thus to more effectively support the medical care.

Fourth Embodiment

Hereinafter, a fourth embodiment will be described in detail.

A factor that affects the fracture in the growth plate of the subject further includes an action of the subject. In the present embodiment, a form will be described in which the medical care support device 10 supports the medical care for the fracture in the growth plate of the subject using the medical information including information on the action of the subject.

A configuration of the medical care support system 1 according to the present embodiment is the same as the configuration of the medical care support system 1 according to the first embodiment (refer to FIG. 1), and a description thereof will be omitted.

Figure 24:
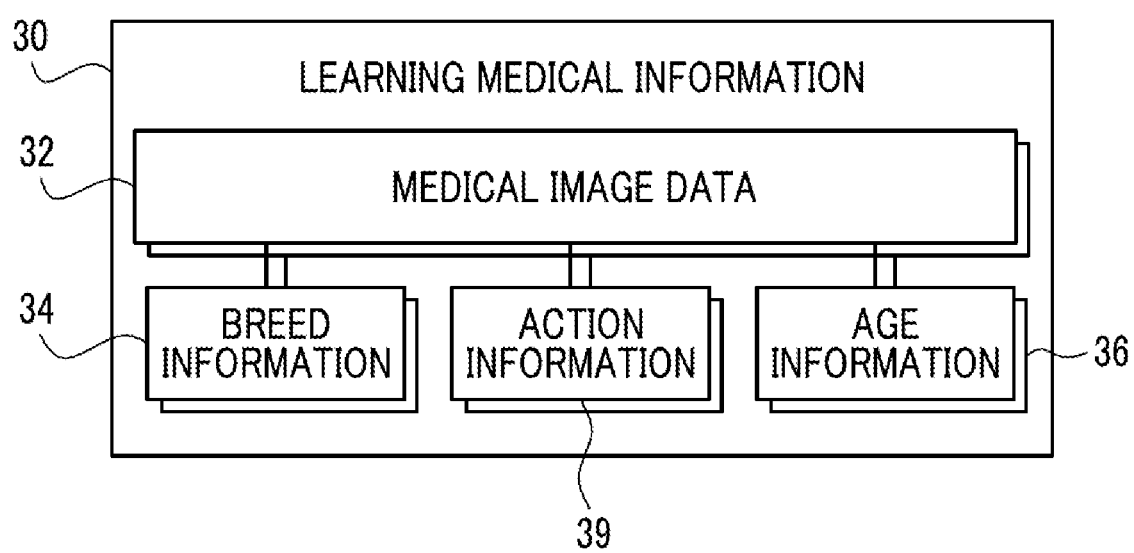
FIG. 24 is a diagram showing an example of learning medical information stored in a storage unit of a medical care support device according to a fourth embodiment.
Figure 25:
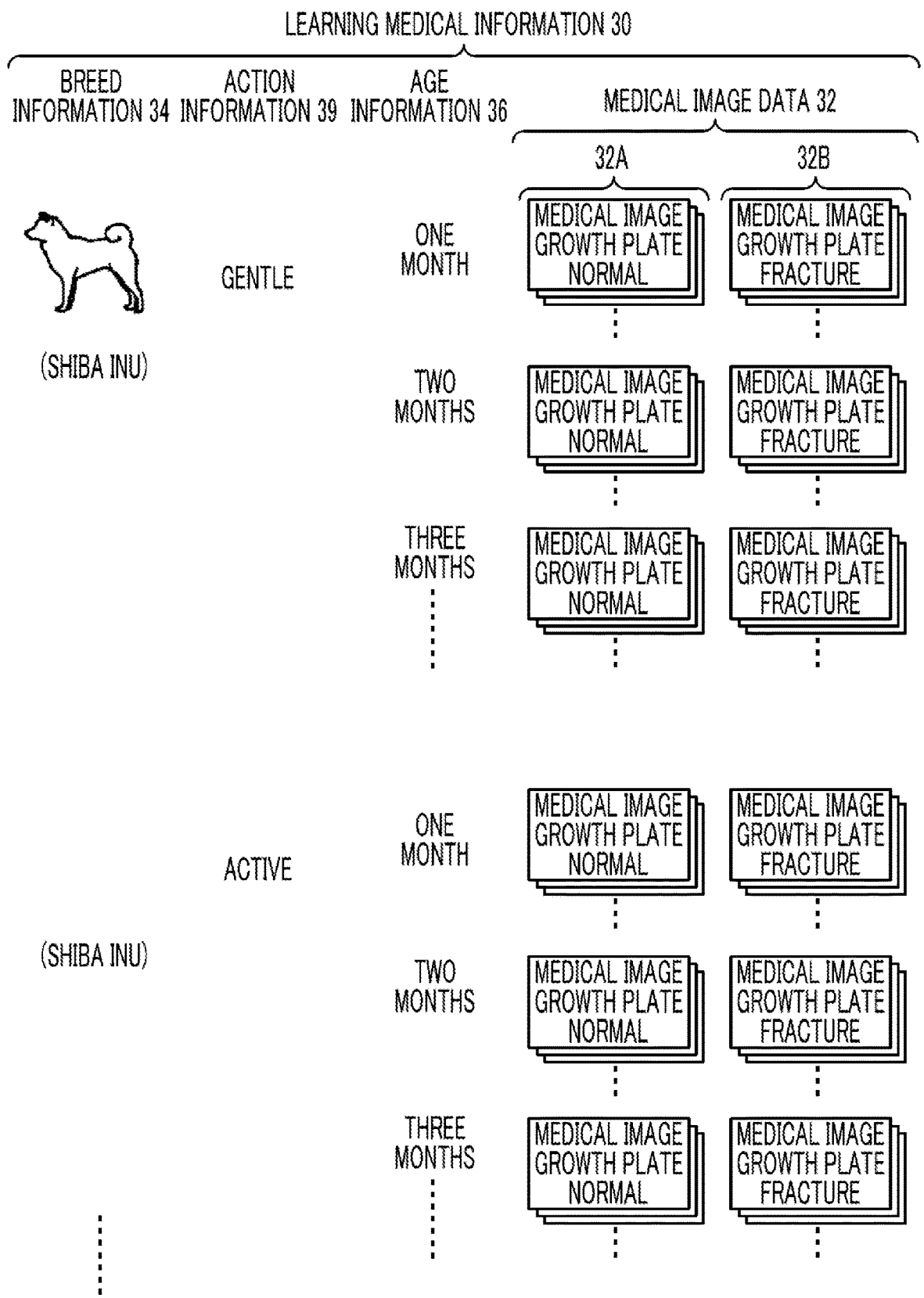
FIG. 25 is a diagram for describing an example of the learning medical information according to the fourth embodiment.

On the other hand, in the medical care support device 10 according to the present embodiment, the contents of the medical information of the subject used for the medical care are different from those of the first embodiment, and the contents of the learning medical information 30 used for learning the learned model 38 are different from those of the first embodiment. Therefore, in the configuration of the medical care support device 10 according to the present embodiment, information included in the learning medical information 30 stored in the storage unit 22 is different from the information (refer to FIGS. 1 and 2) included in the learning medical information 30 stored in the storage unit 22 according to the first embodiment. FIGS. 24 and 25 show an example of the learning medical information 30 according to the present embodiment. As shown in FIGS. 24 and 25, the learning medical information 30 according to the present embodiment includes action information 39 in addition to the breed information 34 (refer to FIGS. 1 and 2) included in the learning medical information 30 according to the first embodiment.

The action information 39 is the information on the action of the subject. Specifically, the action information 39 is information on usual and daily actions of the subject. As an example, in the present embodiment, the information is information representing the normal action of the subject in two stages and, specifically, is information representing whether the action is gentle or active. The action information 39 is not limited to this embodiment and may be information representing the action of the subject in three or more stages. The action information 39 is not limited to the information representing whether the action is gentle or active as in the present embodiment. For example, the information may be any one of information representing whether a frequency of jumping is high or low, a frequency of climbing to a high place such as a sofa or a desk is high or low, and the dog is an indoor dog or an outdoor dog, or may be a combination of these pieces of information.

A method of obtaining the action information 39 is not particularly limited. For example, the user who interprets the medical image represented by the medical image data 32 may input the information on the action of the subject from an operation unit (not shown) of the terminal device 12. For example, in a case where the information on the action of the subject is described in an electronic medical record or the like, the information on the action may be acquired from the electronic medical record or the like in which the information on the action of the subject is described.

Figure 26:
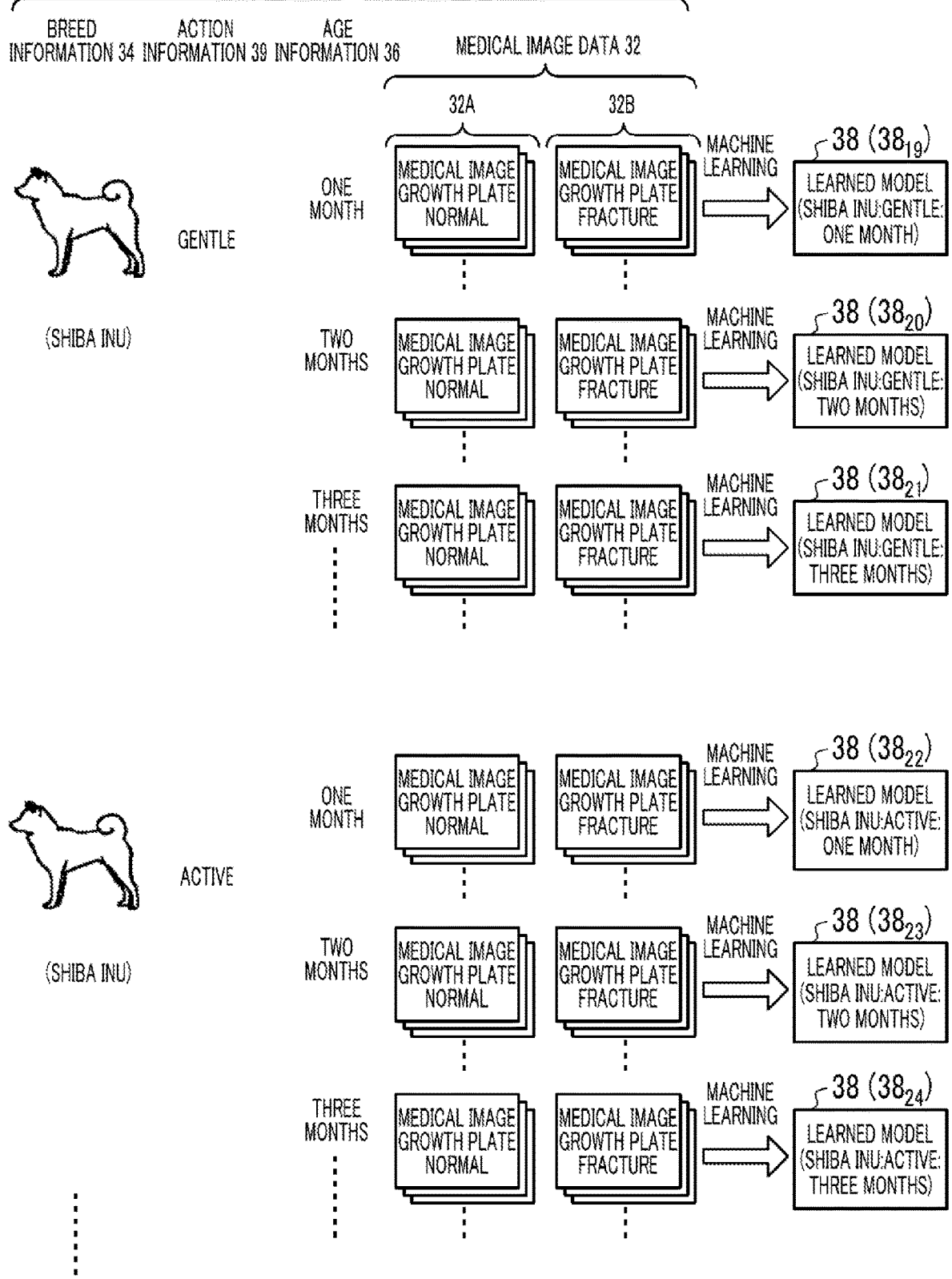
FIG. 26 is a diagram for describing a learned model according to the fourth embodiment.

As shown in FIG. 26, the learned model 38 according to the present embodiment is generated by machine learning using the learning medical information 30 according to the present embodiment. For example, in a case where the dog breed represented by the breed information 34 is "Shiba Inu" and the information on the action represented by the action information 39 is "gentle", a learned model $38_{19}$ for which the dog breed is Shiba Inu, the action is gentle, and the age is one month is generated from the medical image data 32A and 32B whose age represented by the age information 36 is "one month", as shown in FIG. 26. A learned model $38_{20}$ for which the dog breed is Shiba Inu, the action is gentle, and the age is two months is generated from the medical image data 32A and 32B whose age represented by the age information 36 is "two months". A learned model $38_{21}$ for which the dog breed is Shiba Inu, the action is gentle, and the age is three months is generated from the medical image data 32A and 32B whose age represented by the age information 36 is "three months".

For example, in a case where the dog breed represented by the breed information 34 is "Shiba Inu" and the information on the action represented by the action information 39 is "active", a learned model $38_{22}$ for which the dog breed is Shiba Inu, the action is active, and the age is one month is generated from the medical image data 32A and 32B whose age represented by the age information 36 is "one month", as shown in FIG. 26. A learned model $38_{23}$ for which the dog breed is Shiba Inu, the action is active, and the age is two months is generated from the medical image data 32A and 32B whose age represented by the age information 36 is "two months". A learned model $38_{24}$ for which the dog breed is Shiba Inu, the action is active, and the age is three months is generated from the medical image data 32A and 32B whose age represented by the age information 36 is "three months". As described above, an example of the learned model 38 includes a neural network model.

Although FIG. 26 shows the six learned models $38_{19}$ to $38_{24}$, the number of learned models 38 to be generated is not limited to six. In a case where the learned models $38_{19}$ to $38_{24}$ are collectively referred to without distinction, the symbols "19" to "24" for distinguishing the individual models are omitted and the models are referred to as "learned model 38".

Next, a functional configuration of the medical care support device 10 according to the present embodiment in the learning phase will be described. The overall configuration of the medical care support device 10 according to the present embodiment in the learning phase is the same as that of the medical care support device 10 according to the first embodiment (refer to FIG. 6). On the other hand, there is a difference in a specific operation of the learning unit 42 in the medical care support device 10 according to the present embodiment for generating the learned model 38 based on the learning medical information 30. Therefore, the specific operation of the learning unit 42 will be described.

The learning unit 42 according to the present embodiment generates, by machine learning, a plurality of learned models 38 according to combinations of the dog breeds, the actions, and the ages that receive the medical image data 32 to which the fracture presence or absence information is added, for each combination of the dog breed represented by the breed information 34, the information on the action represented by the action information 59, and the age represented by the age information 36, and output the information representing the presence or absence of the fracture in the growth plate in the medical image 33 represented by the medical image data 32.

More specifically, in a case where the medical image data 32A representing the medical image 33A in a non-fractured state among the medical image data 32 to which "Shiba Inu" is added as the dog breed represented by the breed information 34, "gentle" is added as the information on the action represented by the action information 39, and "one month" is added as the age represented by the age information 36 is input, the learning unit 42 causes the model to learn such that information (for example, "0") representing that there is no fracture is output. In a case where the medical image data 32B representing the medical image 33B in a fractured state among the medical image data 32 to which "Shiba Inu" is added as the dog breed represented by the breed information 34, "gentle" is added as the information on the action represented by the action information 39, and "one month" is added as the age represented by the age information 36 is input, the learning unit 42 causes the model to learn such that information (for example, "1") representing that there is the fracture is output. With the learning, the learned model $38_{19}$ for which the dog breed is Shiba Inu, the action is gentle, and the age is one month is generated.

Similarly, in a case where the medical image data 32A representing the medical image 33A in a non-fractured state among the medical image data 32 to which "Shiba Inu" is added as the dog breed represented by the breed information 34, "gentle" is added as the information on the action represented by the action information 39, and "two months" is added as the age represented by the age information 36 is input, the learning unit 42 causes the model to learn such that the information representing that there is no fracture is output. In a case where the medical image data 32B representing the medical image 33B in a fractured state among the medical image data 32 to which "Shiba Inu" is added as the dog breed represented by the breed information 34, "gentle" is added as the information on the action represented by the action information 39, and "two months" is added as the age represented by the age information 36 is input, the learning unit 42 causes the model to learn such that the information representing that there is the fracture is output. With the learning, the learned model $38_{20}$ for which the dog breed is Shiba Inu, the action is gentle, and the age is two months is generated.

Similarly, in a case where the medical image data 32A representing the medical image 33A in a non-fractured state among the medical image data 32 to which "Shiba Inu" is added as the dog breed represented by the breed information 34, "active" is added as the information on the action represented by the action information 39, and "one month" is added as the age represented by the age information 36 is input, the learning unit 42 causes the model to learn such that the information representing that there is no fracture is output. In a case where the medical image data 32B representing the medical image 33B in a fractured state among the medical image data 32 to which "Shiba Inu" is added as the dog breed represented by the breed information 34, "active" is added as the information on the action represented by the action information 39, and "one month" is added as the age represented by the age information 36 is input, the learning unit 42 causes the model to learn such that the information representing that there is the fracture is output. With the learning, the learned model $38_{22}$ for which the dog breed is Shiba Inu, the action is active, the thickness of the bone is thick-boned, and the age is one month is generated.

Figure 27:
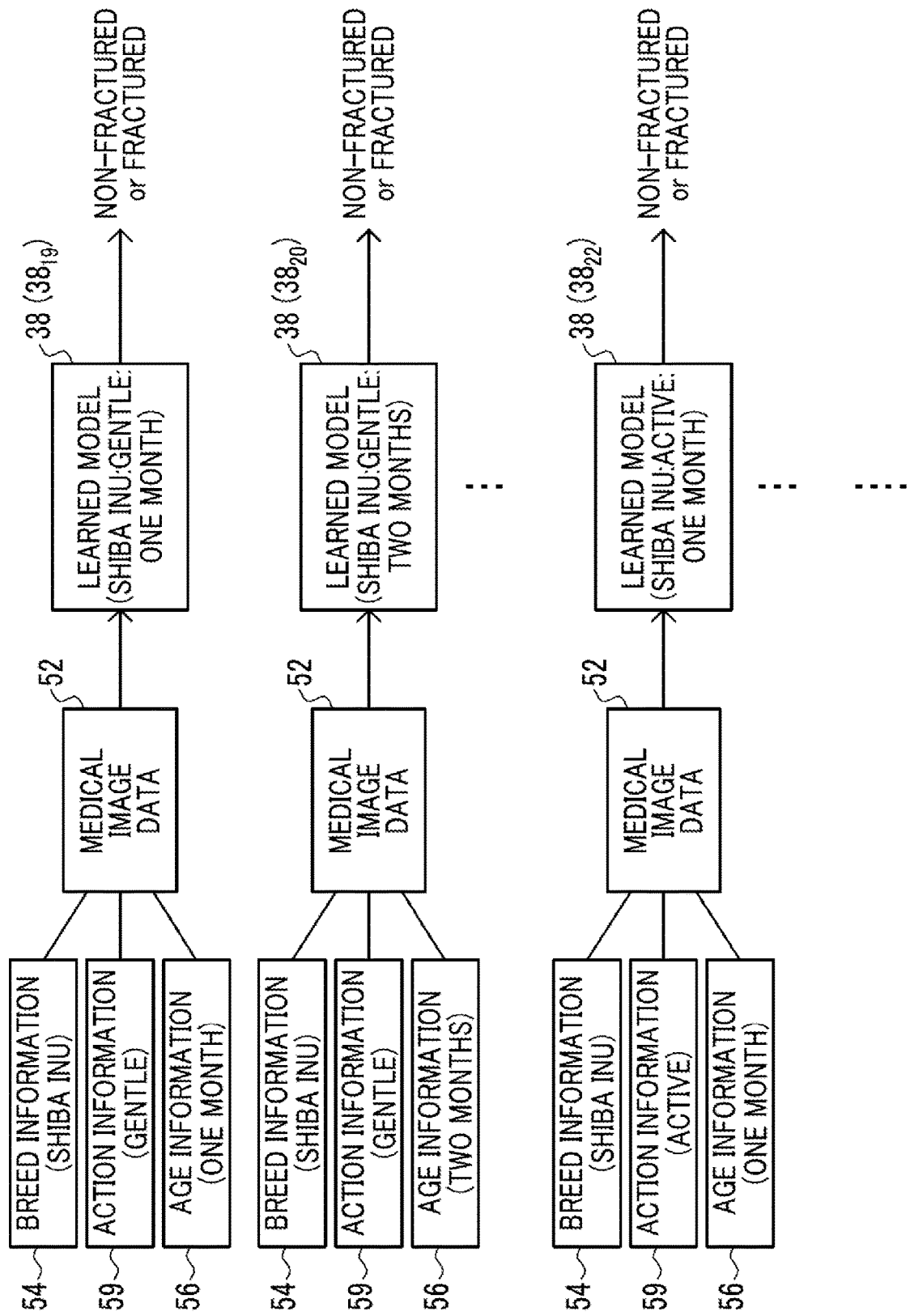
FIG. 27 is a diagram for describing an input and an output of the learned model according to the fourth embodiment.

For example, as described above, the error back propagation method may be employed as an algorithm of the learning by the learning unit 42 described above. As shown in FIG. 27 as an example, the learned model 38 is generated by the learning by the learning unit 42 described above, which receives the medical image data 52, the breed information 54, the action information 59, and the age information 56 for each combination of the dog breed, the action, and the age, and outputs information representing whether there is no fracture or the fracture for the growth plate of the subject appearing in the medical image represented by the input medical image data 52. The learning unit 42 stores the generated learned model 38 in the storage unit 22.

An action of the medical care support device 10 according to the present embodiment in the learning phase, that is, the learning processing executed by the medical care support device 10 is the same as the learning processing (refer to FIG. 8) executed by the medical care support device 10 according to the first embodiment, and thus the description thereof is omitted.

Figure 28:
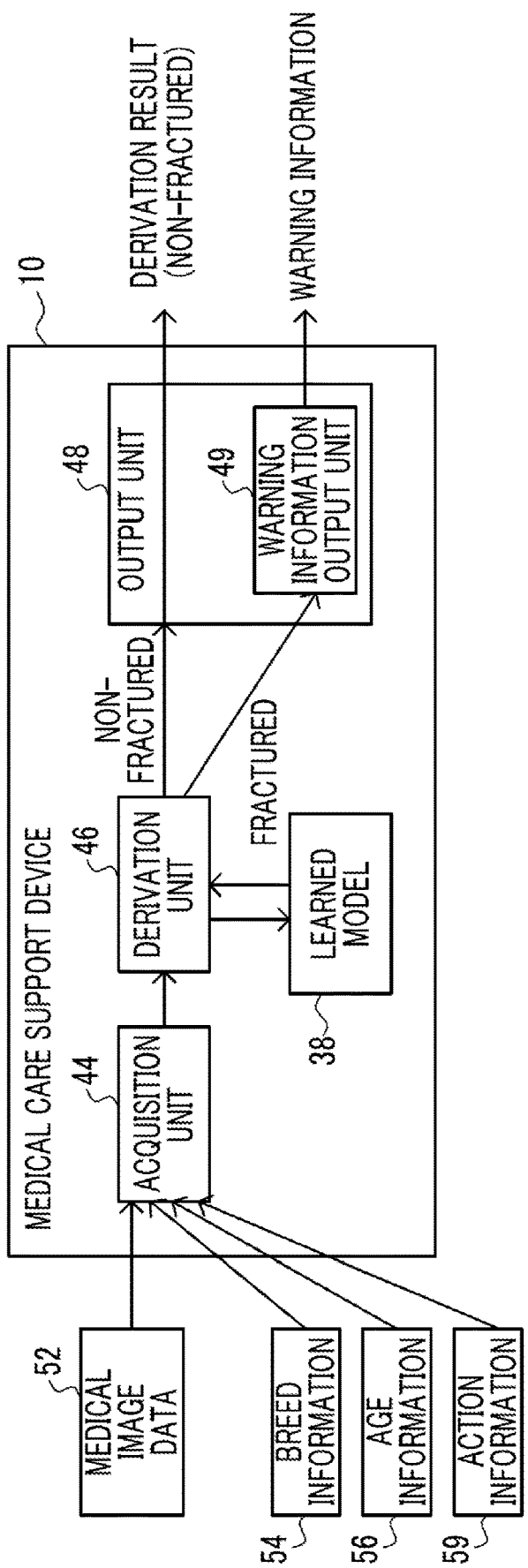
FIG. 28 is a block diagram showing an example of a functional configuration in an operation phase of the medical care support device according to the fourth embodiment.

Next, a functional configuration of the medical care support device 10 according to the present embodiment in the operation phase will be described with reference to FIG. 28. The overall configuration of the medical care support device 10 according to the present embodiment in the operation phase is the same as that of the medical care support device 10 according to the first embodiment (refer to FIG. 9). Specific operations of the acquisition unit 44 and the derivation unit 46 in the medical care support device 10 according to the present embodiment are different. Therefore, the specific operations of the acquisition unit 44 and the derivation unit 46 will be described.

The acquisition unit 44 acquires the medical image data 52 representing the medical image obtained by imaging the subject, the breed information 54 representing the dog breed of the subject, the action information 59 representing information on the action of the subject, and the age information 56 representing the age of the subject as the medical information. Each of the breed information 54, the action information 59, and the age information 56 may be added to the medical image data 52 or may be input by the user through an operation unit (not shown) of the terminal device 12.

The derivation unit 46 derives the presence or absence of the fracture in the growth plate of the subject, based on the medical information (the medical image data 52, the breed information 54, the action information 59, and the age information 56) acquired by the acquisition unit 44 and the learned model 38 learned in advance by the learning medical information 30. Specifically, the derivation unit 46 inputs the medical image data 52 acquired by the acquisition unit 44 to the learned model 38 according to the combination of the dog breed represented by the breed information 54, the action represented by the action information 59, and the age represented by the age information 56 which are acquired by the acquisition unit 44. The learned model 38 outputs the information representing the presence or absence of the fracture in the growth plate of the subject according to the input medical information.

Next, an action of the medical care support device 10 according to the present embodiment in the operation phase will be described. The overall flow of the medical care support processing is the same as the medical care support processing shown in FIG. 10 according to the first embodiment and thus will be described with reference to FIG. 10.

In Step S200, the acquisition unit 44 acquires the medical information of the dog which is the subject and outputs the medical information to the derivation unit 46. Specifically, the acquisition unit 44 acquires the medical image data 52 representing the medical image obtained by imaging the dog of the subject which is the medical care target by the user using the medical image capturing device, the breed information 54 representing the dog breed of the subject, the action information 59 representing the information on the action of the subject, and the age information 56 representing the age of the subject.

In next Step S202, the derivation unit 46 derives the presence or absence of a fracture in the growth plate of the subject, based on the medical information input from the acquisition unit 44 and the learned model 38, as described above. Specifically, the derivation unit 46 inputs the medical image data 52 to the learned model 38 selected according to the combination of the breed information 54, the action information 59, and the age information 56 in the input medical information to acquire the information representing the presence or absence of the fracture in the growth plate of the subject which is output from the learned model 38.

Figure 29:
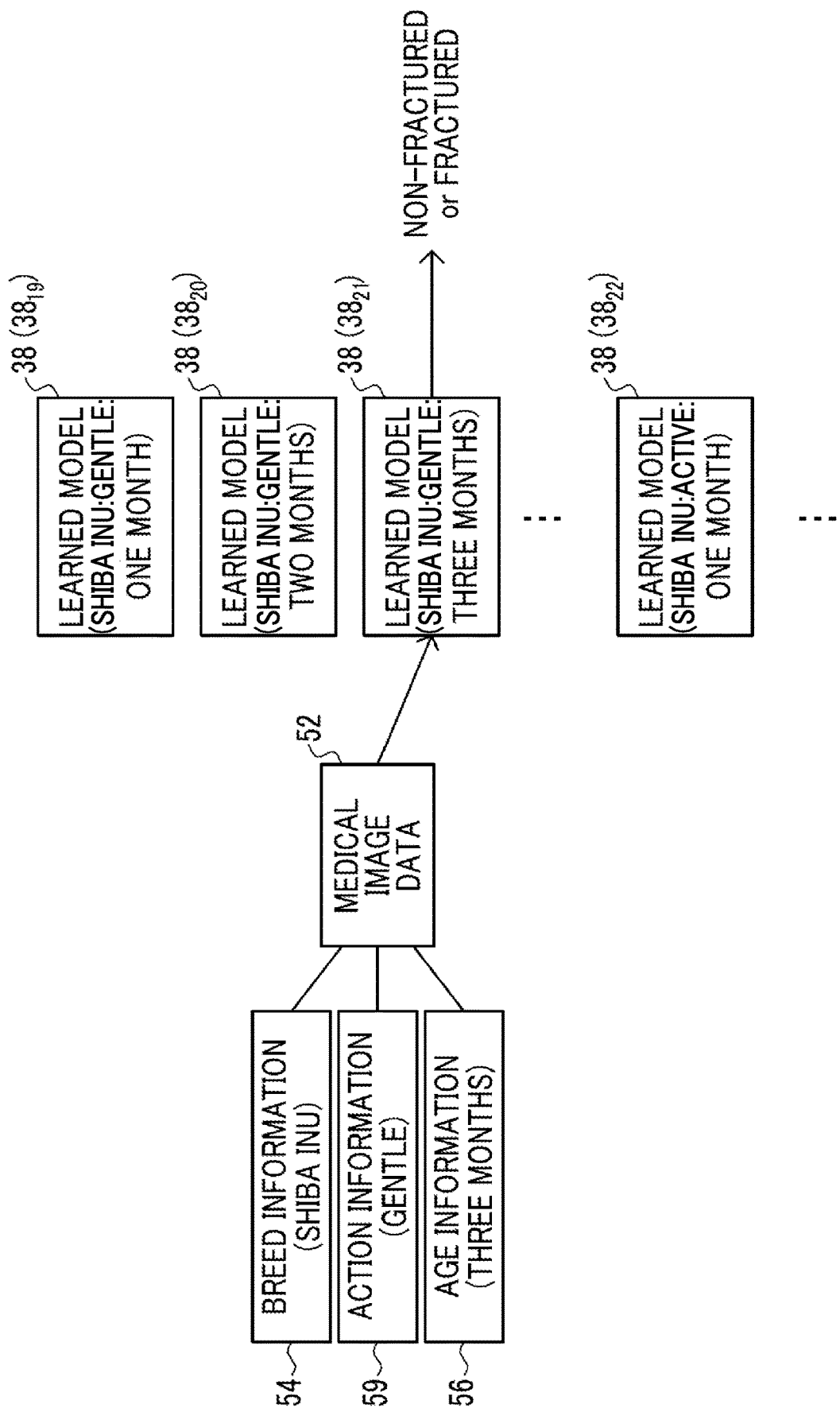
FIG. 29 is a diagram for describing derivation of the presence or absence of a fracture of a growth plate using the learned model according to a combination of a dog breed, an action, and an age in the medical care support device according to the fourth embodiment.

For example, as shown in FIG. 29, in a case where the dog breed represented by the breed information 54 in the medical information is "Shiba Inu", the information on the action represented by the action information 59 is "gentle", and the information represented by the age information 56 is "three months", the derivation unit 46 inputs the medical image data 52 to the learned model $38_{21}$ for which the dog breed is Shiba Inu, the action is gentle, and the age is three months. The information representing the presence or absence of the fracture in the growth plate of the subject is output from the learned model $38_{21}$.

In next Step S204, the derivation unit 46 determines whether or not there is the fracture in the growth plate of the subject as described above. The determination in Step S204 is affirmative in a case where the learned model 38 outputs the information representing that there is the fracture in the growth plate of the subject, the warning information output unit 49 outputs the warning information as described above in next Step S206, and then the medical care support processing ends.

On the other hand, the determination in Step S204 is negative in a case where the learned model 38 outputs the information representing that there is no fracture in the growth plate of the subject, the output unit 48 outputs the derivation result indicating that there is no fracture as described above in next Step S208, and then the medical care support processing ends.

As described above, with the medical care support device 10 according to the present embodiment, the presence or absence of the fracture in the growth plate of the subject is derived based on the medical information including the medical image data 52, the breed information 54, the action information 59, and the age information 56, and the learned model 38. A factor affecting the fracture in the growth plate of the subject includes the action of the subject. For example, there is a known tendency that an active dog is relatively easily fractured and the growth plate thereof is also easily fractured as compared with a gentle dog. For example, a dog that frequently jumps tends to have a fractured growth plate (bone) in a case of landing. For example, a dog having a high frequency of climbing to a high place tends to be more likely to fracture the growth plate (bone) in a case of landing or due to falling.

With the medical care support device 10 according to the present embodiment, the presence or absence of the fracture in the growth plate of the subject is derived using the learned model 38 learned in consideration of the action of the subject which is the factor affecting the fracture in the growth plate. Therefore, it is possible to effectively support the medical care for the fracture in the growth plate using the medical image represented by the medical image data 52.

With the medical care support device 10 according to the present embodiment, even in a case where the subject is a hybrid such as a so-called mixed dog or in a case where the dog breed is unknown, it is possible to derive the presence or absence of the fracture in the growth plate of the subject in consideration of the body type of the subject and thus to more effectively support the medical care.

Fifth Embodiment

Hereinafter, a fifth embodiment will be described in detail.

A configuration of the medical care support system 1 according to the present embodiment is the same as the configuration of the medical care support system 1 according to the first embodiment (refer to FIG. 1), and a description thereof will be omitted.

Figure 30:
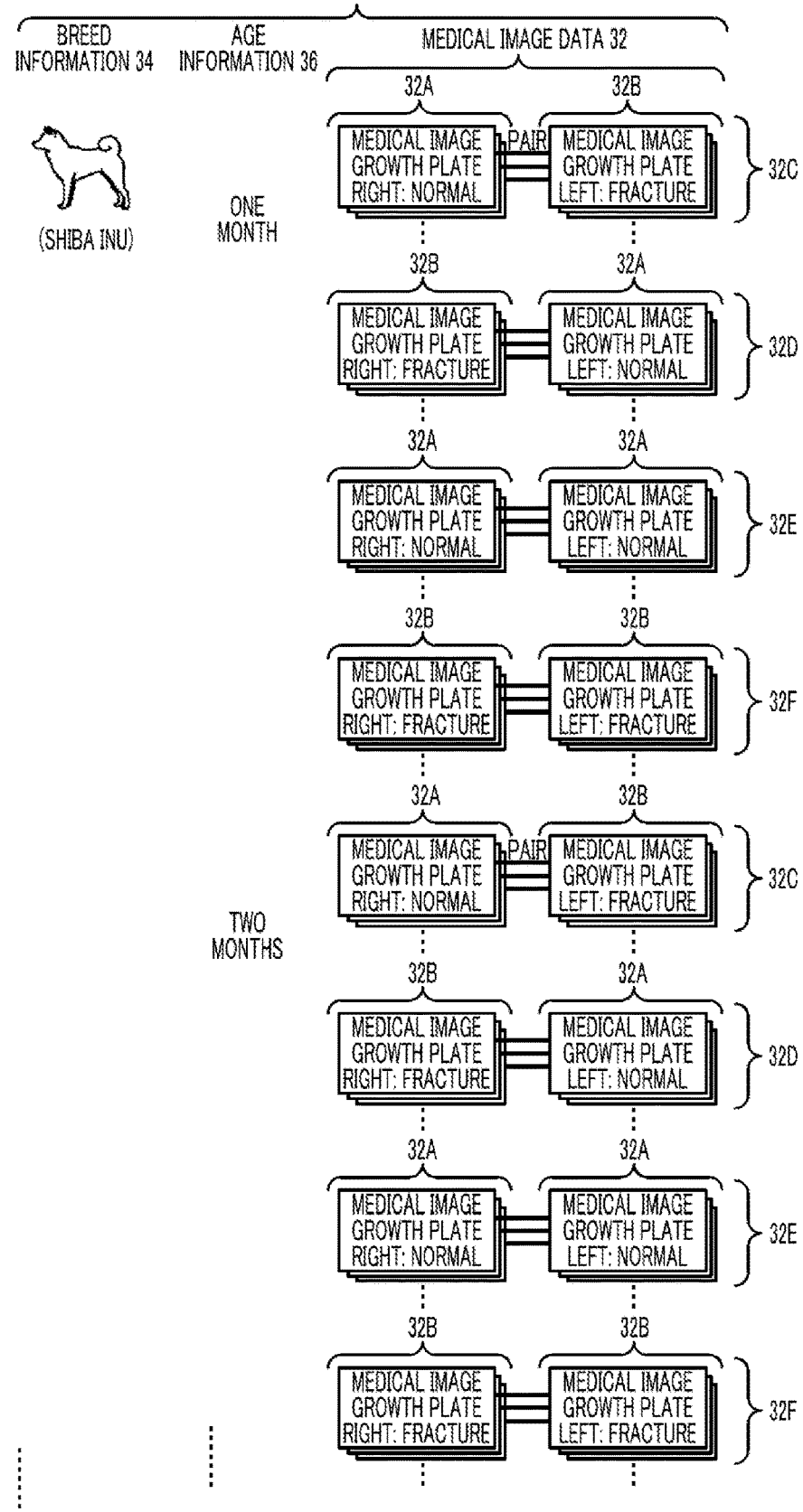
FIG. 30 is a diagram for describing an example of learning medical information according to a fifth embodiment.

On the other hand, in the medical care support device 10 according to the present embodiment, the medical image data 52 of the subject used for the medical care is different from that of the first embodiment, and the medical image data 32 used for learning the learned model 38 is different from that of the first embodiment. FIG. 30 shows an example of the learning medical information 30 including the medical image data 32 according to the present embodiment. As shown in FIG. 30, the medical image data 32 included in the learning medical information 30 according to the present embodiment includes the medical image data 32A representing the medical image 33A in a state where the growth plate is not fractured and the medical image data 32B representing the medical image 33B in a state where the growth plate is fractured, as in the above embodiments.

The medical image data 32 according to the present embodiment uses a pair of two pieces of medical image data representing the medical image of a pair of left and right bones such as a femur as the medical image data 32 for the same subject.

Specifically, the medical image data 32 includes medical image data 32C having the medical image data 32A representing the medical image 33A in a state where the right growth plate is not fractured and the medical image data 32B representing the medical image 33B in a state where the left growth plate is fractured among the growth plates of the pair of left and right bones in the same subject. The medical image data 32 includes medical image data 32D having the medical image data 32B representing the medical image 33B in a state where the right growth plate is fractured and the medical image data 32A representing the medical image 33A in a state where the left growth plate is not fractured among the growth plates of the pair of left and right bones in the same subject. The medical image data 32 includes medical image data 32E having the medical image data 32A representing the medical image 33A in a state where the right growth plate is not fractured and the medical image data 32A representing the medical image 33A in a state where the left growth plate is not fractured among the growth plates of the pair of left and right bones in the same subject. The medical image data 32 includes medical image data 32F having the medical image data 32B representing the medical image 33B in a state where the right growth plate is fractured and the medical image data 32B representing the medical image 33B in a state where the left growth plate is fractured among the growth plates of the pair of left and right bones in the same subject.

In other words, the medical image data 32 includes the medical image data 32C in which the right side of the pair is not fractured and the left side thereof is fractured, the medical image data 32D in which the right side of the pair is fractured and the left side thereof is not fractured, the medical image data 32E in which both sides of the pair are not fractured, and the medical image data 32F in which both sides of the pair are fractured. The medical image data 32B according to the present embodiment is an example of the first medical image data in which the growth plate of one bone of the present disclosure is fractured, and the medical image data 32A is an example of the second medical image data in which the growth plate of the other bone of the present disclosure is not fractured.

The medical image data 32 according to the present embodiment includes the medical image data 32E including a plurality of pairs in which the right growth plate is not fractured and the medical image data 32F including a plurality of pairs in which both left and right growth plates are fractured, but may not include these pieces of medical image data. The medical image data 32 may include a pair of the medical image data 32A representing the medical image 33A in a state where the growth plate is not fractured and the medical image data 32B representing the medical image 33B in a state where the growth plate is fractured among the pair of left and right medical image data 32.

Figure 31:
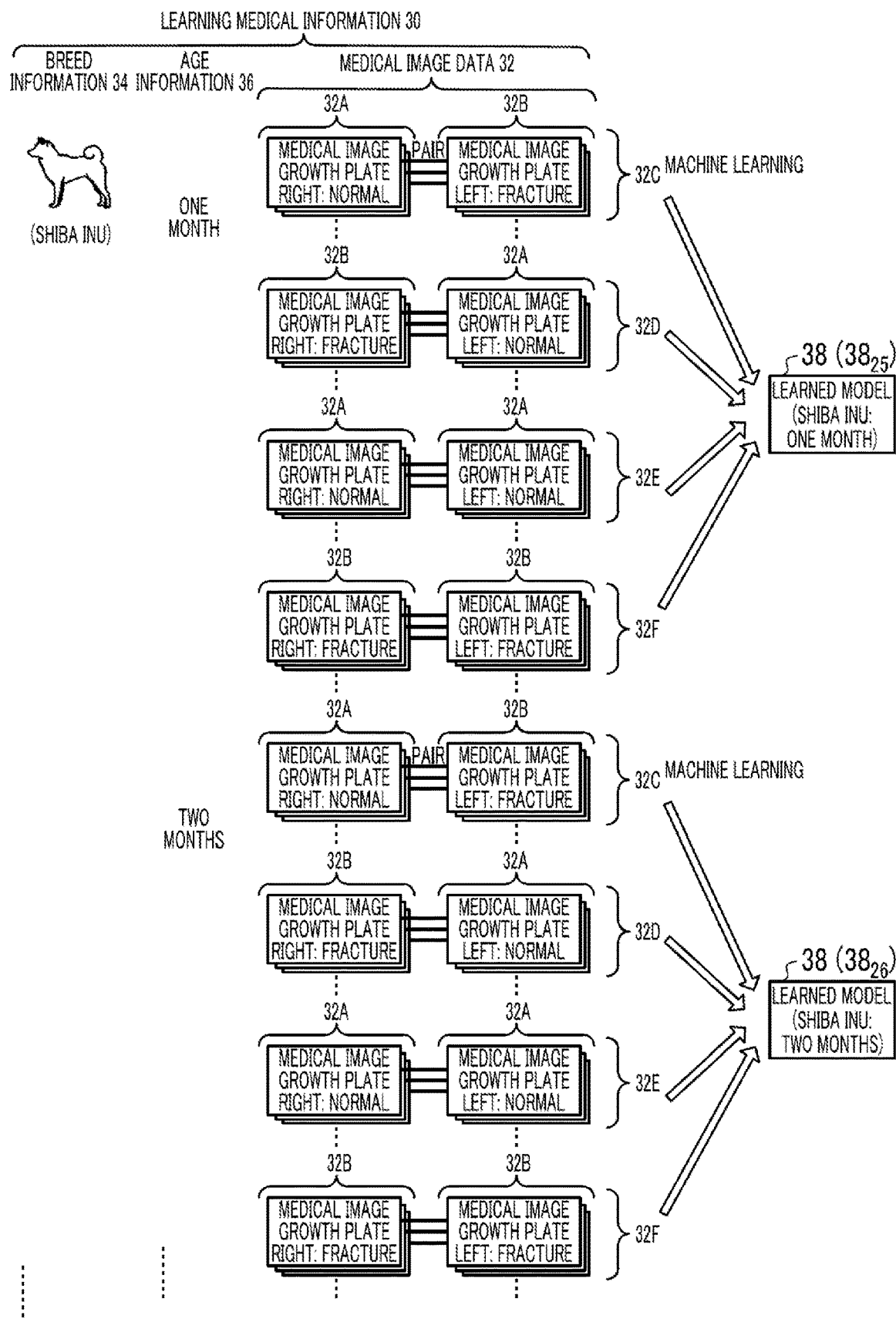
FIG. 31 is a diagram for describing a learned model according to the fifth embodiment.

As shown in FIG. 31, the learned model 38 according to the present embodiment is generated by machine learning using the learning medical information 30 according to the present embodiment. For example, in a case where the dog breed represented by the breed information 34 is "Shiba Inu", a learned model $38_{25}$ for which the dog breed is Shiba Inu and the age is one month is generated from the medical image data 32C, 32D, 32E, and 32F whose age represented by the age information 36 is "one month", as shown in FIG. 31. A learned model $38_{26}$ for which the dog breed is Shiba Inu and the age is two months is generated from the medical image data 32C, 32D, 32E, and 32F whose age represented by the age information 36 is "two months".

Although FIG. 31 shows the two learned models $38_{25}$ and $38_{26}$, the number of learned models 38 to be generated is not limited to two. In a case where the learned models $38_{25}$ and $38_{26}$ are collectively referred to without distinction, the symbols "25" and "26" for distinguishing the individual models are omitted and the models are referred to as "learned model 38".

Next, a functional configuration of the medical care support device 10 according to the present embodiment in the learning phase will be described. The overall configuration of the medical care support device 10 according to the present embodiment in the learning phase is the same as that of the medical care support device 10 according to the first embodiment (refer to FIG. 6). On the other hand, there is a difference in a specific operation of the learning unit 42 in the medical care support device 10 according to the present embodiment for generating the learned model 38 based on the learning medical information 30. Therefore, the specific operation of the learning unit 42 will be described.

The learning unit 42 according to the present embodiment generates, by machine learning, a plurality of learned models 38 according to combinations of the dog breeds and the ages that receive the medical image data 32 including the medical image data 32C, 32D, 32E, and 32F to which fracture presence or absence information is added, for each combination of the dog breed represented by the breed information 34 and the age represented by the age information 36, and output the information representing the presence or absence of the fracture in the left and right growth plates in the medical image 33 represented by the medical image data 32.

More specifically, in a case where the medical image data 32C in which the right side of the pair is not fractured and the left side thereof is fractured among the medical image data 32 to which "Shiba Inu" is added as the dog breed represented by the breed information 34 and "one month" is added as the age represented by the age information 36 is input, the learning unit 42 causes the model to learn such that information (for example, "10") representing that the left side thereof is fractured is output. In a case where the medical image data 32D in which the right side of the pair is fractured and the left side thereof is not fractured among the medical image data 32 to which "Shiba Inu" is added as the dog breed represented by the breed information 34 and "one month" is added as the age represented by the age information 36 is input, the learning unit 42 causes the model to learn such that information (for example, "01") representing that the right side thereof is fractured is output. In a case where the medical image data 32E in which both sides of the pair are not fractured among the medical image data 32 to which "Shiba Inu" is added as the dog breed represented by the breed information 34 and "one month" is added as the age represented by the age information 36 is input, the learning unit 42 causes the model to learn such that information (for example, "00") representing that both left and right sides thereof are not fractured is output. In a case where the medical image data 32F in which both sides of the pair are fractured among the medical image data 32 to which "Shiba Inu" is added as the dog breed represented by the breed information 34 and "one month" is added as the age represented by the age information 36 is input, the learning unit 42 causes the model to learn such that information (for example, "11") representing that both left and right sides are fractured is output. With the learning, the learned model $38_{25}$ for which the dog breed is Shiba Inu and the age is one month is generated.

Similarly, in a case where the medical image data 32C in which the right side of the pair is not fractured and the left side thereof is fractured among the medical image data 32 to which "Shiba Inu" is added as the dog breed represented by the breed information 34 and "two months" is added as the age represented by the age information 36 is input, the learning unit 42 causes the model to learn such that the information representing that the left side thereof is fractured is output. In a case where the medical image data 32D in which the right side of the pair is fractured and the left side thereof is not fractured among the medical image data 32 to which "Shiba Inu" is added as the dog breed represented by the breed information 34 and "two months" is added as the age represented by the age information 36 is input, the learning unit 42 causes the model to learn such that the information representing that the right side thereof is fractured is output. In a case where the medical image data 32E in which both sides of the pair are not fractured among the medical image data 32 to which "Shiba Inu" is added as the dog breed represented by the breed information 34 and "two months" is added as the age represented by the age information 36 is input, the learning unit 42 causes the model to learn such that the information representing that both left and right sides thereof are not fractured is output. In a case where the medical image data 32F in which both sides of the pair are fractured among the medical image data 32 to which "Shiba Inu" is added as the dog breed represented by the breed information 34 and "two months" is added as the age represented by the age information 36 is input, the learning unit 42 causes the model to learn such that the information representing that both left and right sides are fractured is output. With the learning, the learned model $38_{26}$ for which the dog breed is Shiba Inu and the age is two months is generated.

Figure 32:
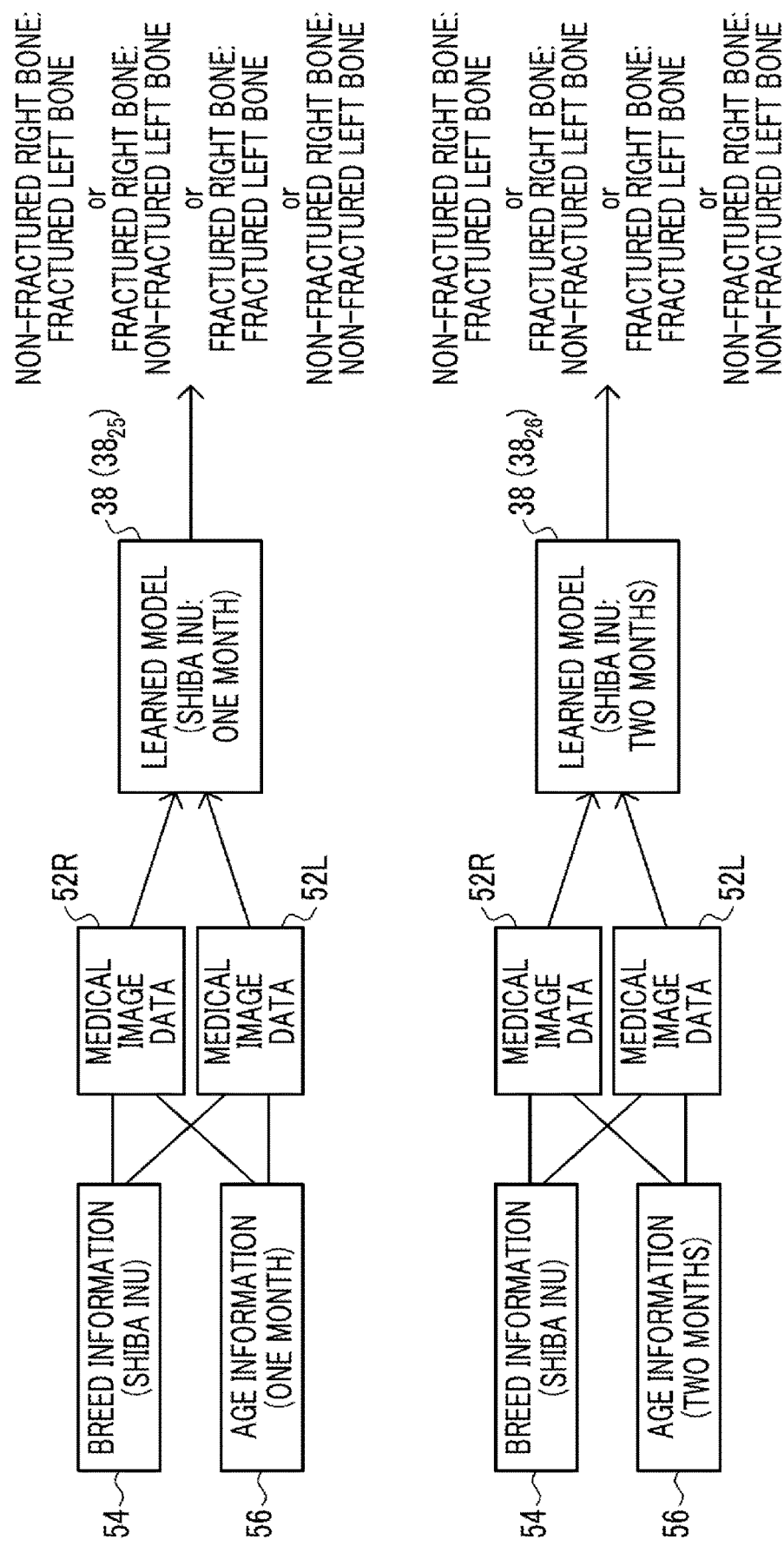
FIG. 32 is a diagram for describing an input and an output of the learned model according to the fifth embodiment.

For example, as described above, the error back propagation method may be employed as an algorithm of the learning by the learning unit 42 described above. As shown in FIG. 32 as an example, the learned model 38 is generated by the learning by the learning unit 42 described above, which receives medical image data 52R representing the medical image obtained by imaging the right bone of the pair of bones of the subject and medical image data 52L representing the medical image obtained by imaging the left bone thereof, the breed information 54, and the age information 56 for each combination of the dog breed and the age, and outputs information representing whether there is no fracture or the fracture for each of the left and right growth plates of the subject appearing in a medical image respectively represented by the input medical image data 52R and 52L. The learning unit 42 stores the generated learned model 38 in the storage unit 22.

An action of the medical care support device 10 according to the present embodiment in the learning phase, that is, the learning processing executed by the medical care support device 10 is the same as the learning processing (refer to FIG. 8) executed by the medical care support device 10 according to the first embodiment, and thus the description thereof is omitted.

Figure 33:
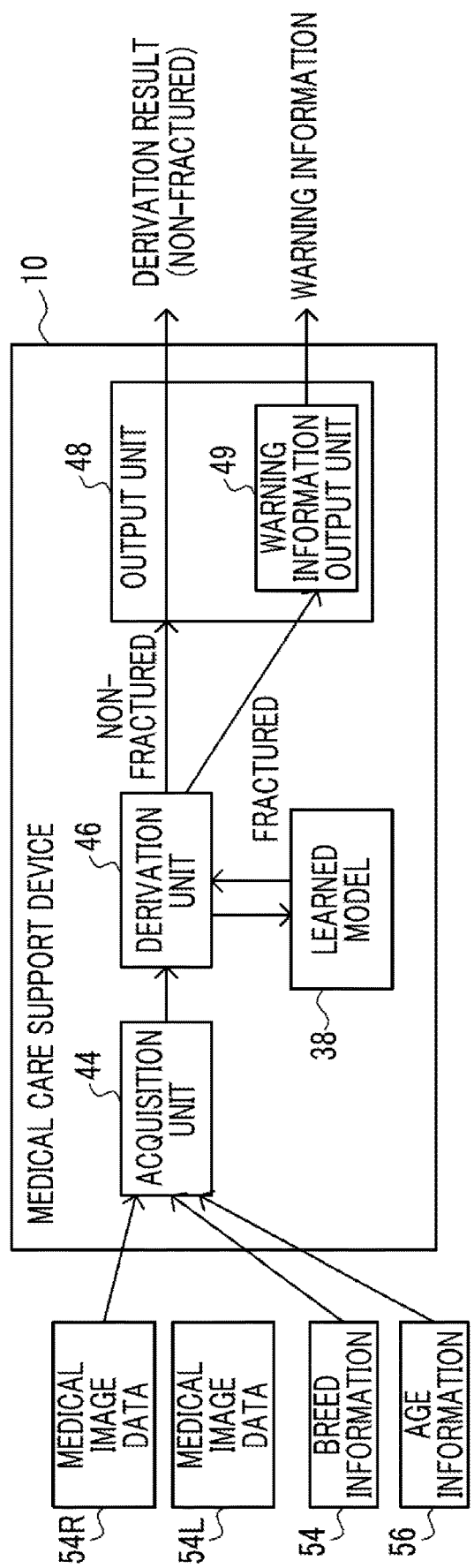
FIG. 33 is a block diagram showing an example of a functional configuration in an operation phase of a medical care support device according to the fifth embodiment.

Next, a functional configuration of the medical care support device 10 according to the present embodiment in the operation phase will be described with reference to FIG. 33. The overall configuration of the medical care support device 10 according to the present embodiment in the operation phase is the same as that of the medical care support device 10 according to the first embodiment (refer to FIG. 9). Specific operations of the acquisition unit 44 and the derivation unit 46 in the medical care support device 10 according to the present embodiment are different. Therefore, the specific operations of the acquisition unit 44 and the derivation unit 46 will be described.

The acquisition unit 44 acquires the medical image data 52R representing the medical image obtained by imaging the right bone of the pair of bones of the subject, the medical image data 52L representing the medical image obtained by imaging the left bone thereof, and the breed information 54 representing the dog breed of the subject, and the age information 56 representing the age of the subject as the medical information. Each of the breed information 54 and the age information 56 may be added to at least one of the medical image data 52R or 52L, or may be input by the user through an operation unit (not shown) of the terminal device 12.

The derivation unit 46 derives the presence or absence of the fracture in the growth plate of the subject, based on the medical information (the medical image data 52R and 52L, the breed information 54, and the age information 56) acquired by the acquisition unit 44 and the learned model 38 learned in advance by the learning medical information 30. Specifically, the derivation unit 46 inputs the medical image data 52R and 52L acquired by the acquisition unit 44 to the learned model 38 according to the combination of the dog breed represented by the breed information 54 and the age represented by the age information 56 which are acquired by the acquisition unit 44. The learned model 38 outputs the information representing the presence or absence of the fracture for each of the left and right growth plates of the subject according to the input medical information.

Next, an action of the medical care support device 10 according to the present embodiment in the operation phase will be described. The overall flow of the medical care support processing is the same as the medical care support processing shown in FIG. 10 according to the first embodiment and thus will be described with reference to FIG. 10.

In Step S200, the acquisition unit 44 acquires the medical information of the dog which is the subject and outputs the medical information to the derivation unit 46. Specifically, the acquisition unit 44 acquires the medical image data 52R and 52L representing the pair of medical images obtained by imaging each of the left and the right of one bone of the dog of the subject which is the medical care target by the user using the medical image capturing device, the breed information 54 representing the dog breed of the subject, the action information 59 representing the information on the action of the subject, and the age information 56 representing the age of the subject.

In next Step S202, the derivation unit 46 derives the presence or absence of the fracture for each of the left and right growth plates of the subject based on the medical information input from the acquisition unit 44 and the learned model 38, as described above. Specifically, the derivation unit 46 inputs the medical image data 52R and 52L to the learned model 38 selected according to the combination of the breed information 54 and the age information 56 in the input medical information to acquire the information representing the presence or absence of the fracture in each of the left and right growth plates of the subject which are output from the learned model 38.

Figure 34:
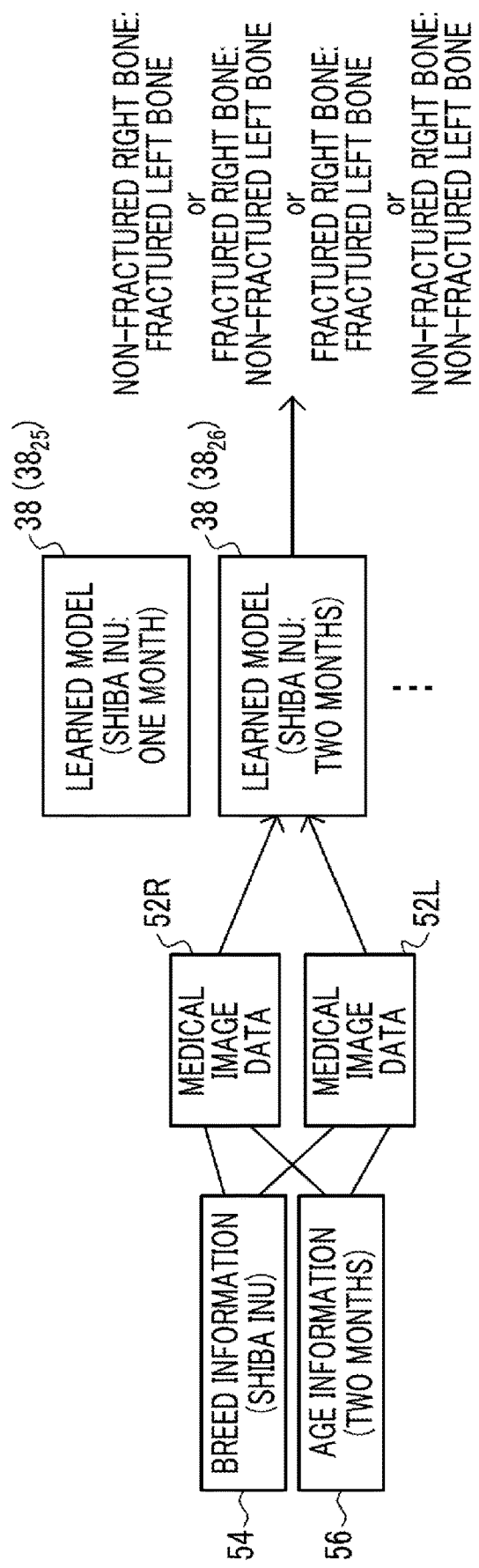
FIG. 34 is a diagram for describing derivation of the presence or absence of a fracture in each of left and right growth plates using the learned model according to a combination of a dog breed and an age in the medical care support device according to the fifth embodiment.

For example, as shown in FIG. 34, in a case where the dog breed represented by the breed information 54 in the medical information is "Shiba Inu" and the information represented by the age information 56 is "one month", the derivation unit 46 inputs the medical image data 52R and 52L to the learned model $38_{26}$ for which the dog breed is Shiba Inu and the age is two months. The information representing the presence or absence of the fracture in each of the left and right growth plates of the subject is output from the learned model $38_{26}$.

In next Step S204, the derivation unit 46 determines whether or not there is the fracture in each of the left and right growth plates of the subject as described above. The determination in Step S204 is affirmative in a case where the learned model 38 outputs the information representing that there is the fracture in at least one of the left growth plate or the right growth plate of the subject, the warning information output unit 49 outputs the warning information as described above in next Step S206, and then the medical care support processing ends. In this case, it is preferable that the warning information output unit 49 also outputs information representing whether the growth plate having the fracture is left or right (or both) based on the output result of the learned model 38.

On the other hand, the determination in Step S204 is negative in a case where the learned model 38 outputs the information representing that there is no fracture in any of the left and right growth plates of the subject, the output unit 48 outputs the derivation result indicating that there is no fracture as described above in next Step S208, and then the medical care support processing ends.

As described above, with the medical care support device 10 according to the present embodiment, the presence or absence of the fracture in the growth plate of the subject is derived based on the medical information including the medical image data 52R and 52L, the breed information 54, and the age information 56, and the learned model 38. In a case where one of the pair of left and right bones in the same subject is fractured, the medical image obtained by imaging the fractured bone of the pair is compared with the medical image obtained by imaging the non-fractured bone thereof and thus it is possible to perform the medical care for the presence or absence of the fracture or the state of the fracture with higher accuracy.

With the medical care support device 10 according to the present embodiment, the presence or absence of the fracture in the growth plate of the subject is derived using the learned model 38 learned using the medical image data 52R and 52L of each of the left and the right of one bone. Therefore, it is possible to perform the medical care for the fracture in the growth plate using the medical image represented by the medical image data 52 with higher accuracy.

As described above, the medical care support device 10 according to the above embodiments comprises the acquisition unit 44, the derivation unit 46, and the warning information output unit 49. The acquisition unit 44 acquires the medical information including the medical image data 52 representing the medical image obtained by imaging the bone of the subject and the age information 56 representing the age of the subject in a case where the medical image 33 is imaged. The derivation unit 46 derives the presence or absence of the fracture in the growth plate 60 of the subject based on the medical information acquired by the acquisition unit 44 and the learned model 38 learned in advance using a plurality of pieces of learning medical information 30 including the medical image data 32 and the age information 36. The warning information output unit 49 outputs warning information representing a warning in a case where the growth plate of the subject is fractured.

As described above, the growth plate is the tissue that is fragile and easily fractured in a case where impact is applied. In a case where the growth of the bone is hindered by the fracture in the growth plate, the subject may experience symptoms such as shortening or bending of the bone and causing persistent pain. Therefore, in a case where the growth plate is fractured, it is important to perform appropriate medical treatment at an early stage. In particular, in the case where the subject is an animal such as a dog or a cat, unlike a human, the subject grows faster than the human. Therefore, it is desired to detect the fracture earlier and perform appropriate medical treatment.

With the medical care support device 10 according to the above embodiments, the presence or absence of the fracture in the growth plate of the subject is derived based on the medical information including the medical image data 52 and the age information 56, and the learned model 38. Therefore, with the medical care support device 10 according to the present embodiment, it is possible to effectively support the medical care for the fracture in the growth plate using the medical image. With the medical care support device 10 according to the present embodiment, it is possible to perform the medical care for the fracture in the growth plate more appropriately and thus to promote smooth growth of the subject.

In the medical care support device 10 according to the above embodiments, the learned model 38 outputs the information representing the presence or absence of the fracture in the growth plate is described. However, the information output from the learned model 38 is not limited to the present embodiment.

For example, a Salter-Harris classification is known in which the fracture in the growth plate is classified into five types from type I to type V shown in FIG. 35 as a classification of the fracture in the growth plate. Therefore, in a case where the growth plate is fractured, information representing which of the above classifications the fracture corresponds to may be output from the learned model 38. In this case, the learned model 38 may be generated using the learning medical information 30 that further includes the information representing which of the above classifications the fracture in the medical image data 32B corresponds to.

Various types of information included in the learning medical information 30 used for generating the learned model 38 are not limited to the above embodiments. For example, the learning medical information 30 in the above embodiments may be combined. Further, for example, the learning medical information 30 may include bone type information representing a type of bone having the growth plate. For example, in a case where the medical image data 32B represents the medical image 33 in a state where the growth plate of the distal femoral epiphysis is fractured, the learning medical information 30 may include the bone type information representing the distal femoral epiphysis.

Further, in the above embodiments, the dog is employed as the subject is described, but the subject is not limited thereto. For example, a human may be employed as the subject, or an animal other than a dog such as a cat may be employed.

The following various processors may be used as a hardware structure of a processing unit that executes various types of processing such as each functional unit of the medical care support device 10 in the above embodiments. The various processors include a programmable logic device (PLD) which is a processor whose circuit configuration is changeable after manufacturing such as a field-programmable gate array (FPGA), a dedicated electric circuit which is a processor having a circuit configuration exclusively designed to execute specific processing such as an application specific integrated circuit (ASIC), and the like, in addition to the CPU which is a general-purpose processor that executes software (program) to function as various processing units as described above.

One processing unit may be configured by one of the various processors or a combination of two or more processors of the same type or different types (for example, a combination of a plurality of FPGAs or a combination of a CPU and an FPGA). A plurality of processing units may be configured by one processor.

As an example of configuring the plurality of processing units with one processor, first, there is a form in which one processor is configured by a combination of one or more CPUs and software and the processor functions as the plurality of processing units, as represented by computers such as a client and a server. Second, there is a form in which a processor that realizes the functions of the entire system including the plurality of processing units with one integrated circuit (IC) chip is used, as represented by a system-on-chip (SoC) or the like. As described above, the various processing units are configured using one or more of the various processors as the hardware structure.

Further, more specifically, a circuitry combining circuit elements such as semiconductor elements can be used as the hardware structure of the various processors.

Further, in the above embodiment, the learning program 23A and the medical care support program 23B are stored (installed) in the storage unit 22 in advance is described, but the present disclosure is not limited thereto. Each of the learning program 23A and the medical care support program 23B may be provided in a form of being recorded on a recording medium such as a compact disc read only memory (CD-ROM), a digital versatile disc read only memory (DVD-ROM), and a Universal Serial Bus (USB) memory. Each of the learning program 23A and the medical care support program 23B may be configured to be downloaded from an external device through a network.

The following appendix is disclosed with regard to the above embodiment.

Appendix 1

A medical care support device comprising:
an acquisition unit that acquires learning medical information including medical image data representing a medical image obtained by imaging a bone of a subject and age information representing an age of the subject in a case where the medical image is imaged; and
a learning unit that generates a learned model that outputs information representing presence or absence of a fracture in a growth plate of the subject, based on the medical image data and the age information with learning of the learning medical information as learning data.

What is claimed is:

1. A medical care support device comprising:
a processor configured to:
acquire medical information including medical image data representing a medical image obtained by imaging a bone of a subject and age information representing an age of the subject in a case where the medical image is imaged by a medical image capture;
derive presence or absence of a fracture in a growth plate of the subject, based on the acquired medical information and a learned model learned in advance using a plurality of pieces of learning medical information including the medical image data and the age information; and
output, to a terminal, warning information representing a warning in a case where the growth plate of the subject is fractured,
wherein the medical information further includes breed information representing a breed of the subject, and
wherein the learning medical information further includes the breed information.

2. The medical care support device according to claim 1, wherein the medical information further includes thickness information representing a thickness of the bone of the subject, and
wherein the learning medical information further includes the thickness information.

3. The medical care support device according to claim 1, wherein the medical information further includes body type information on a body type of the subject, and
wherein the learning medical information further includes the body type information.

4. The medical care support device according to claim 1, wherein the medical information further includes action information on an action of the subject, and
wherein the learning medical information further includes the action information.

5. The medical care support device according to claim 1, wherein the medical image data included in the learning medical information includes first medical image data representing a first medical image in which the growth plate is fractured and second medical image data representing a second medical image in which the growth plate is not fractured.

6. The medical care support device according to claim 1, wherein the medical image data included in the learning medical information includes, out of the growth plates in a pair of left and right bones, first medical image data in which the growth plate of one bone is fractured and second medical image data in which the growth plate of the other bone is not fractured, and
wherein the processor is further configured to acquire the medical image data representing the medical image obtained by imaging each of the pair of left and right bones as the medical image data of the subject.

7. A medical care support method executed by a computer, comprising:
acquiring medical information including medical image data representing a medical image obtained by imaging a bone of a subject and age information representing an age of the subject in a case where the medical image is imaged;

deriving presence or absence of a fracture in a growth plate of the subject, based on the acquired medical information and a learned model learned in advance using a plurality of pieces of learning medical information including the medical image data and the age information; and outputting, to a terminal, warning information representing a warning in a case where the growth plate of the subject is fractured, wherein the medical information further includes breed information representing a breed of the subject, and wherein the learning medical information further includes the breed information.

8. A non-transitory computer-readable storage medium storing a medical care support program causing a computer to execute the following processing of:

acquiring medical information including medical image data representing a medical image obtained by imaging a bone of a subject and age information representing an age of the subject in a case where the medical image is imaged;

deriving presence or absence of a fracture in a growth plate of the subject, based on the acquired medical information and a learned model learned in advance using a plurality of pieces of learning medical information including the medical image data and the age information; and outputting, to a terminal, warning information representing a warning in a case where the growth plate of the subject is fractured, wherein the medical information further includes breed information representing a breed of the subject, and wherein the learning medical information further includes the breed information.

* * * * *